(12) United States Patent
Nagai et al.

(10) Patent No.: US 10,894,770 B2
(45) Date of Patent: Jan. 19, 2021

(54) FULLERENE DERIVATIVE AND N-TYPE SEMICONDUCTOR MATERIAL

(71) Applicants: DAIKIN INDUSTRIES, LTD., Osaka (JP); OSAKA UNIVERSITY, Osaka (JP)

(72) Inventors: Takabumi Nagai, Osaka (JP); Kenji Adachi, Osaka (JP); Yoshio Aso, Osaka (JP); Yutaka Ie, Osaka (JP); Makoto Karakawa, Osaka (JP)

(73) Assignees: DAIKIN INDUSTRIES, LTD., Osaka (JP); OSAKA UNIVERSITY, Osaka (JP)

( * ) Notice: Subject to any disclaimer, the term of this patent is extended or adjusted under 35 U.S.C. 154(b) by 117 days.

(21) Appl. No.: 15/766,148

(22) PCT Filed: Oct. 6, 2016

(86) PCT No.: PCT/JP2016/079795
§ 371 (c)(1),
(2) Date: Apr. 5, 2018

(87) PCT Pub. No.: WO2017/061543
PCT Pub. Date: Apr. 13, 2017

(65) Prior Publication Data
US 2018/0282274 A1    Oct. 4, 2018

(30) Foreign Application Priority Data
Oct. 6, 2015    (JP) .................................. 2015-198877

(51) Int. Cl.
| | | |
|---|---|---|
| *C07D 209/52* | (2006.01) | |
| *C01B 32/154* | (2017.01) | |
| *H01L 31/0216* | (2014.01) | |
| *H01L 51/00* | (2006.01) | |
| *H01L 51/42* | (2006.01) | |
| *H01L 51/44* | (2006.01) | |

(52) U.S. Cl.
CPC .......... *C07D 209/52* (2013.01); *C01B 32/154* (2017.08); *H01L 31/02167* (2013.01); *H01L 51/0047* (2013.01); *H01L 51/4253* (2013.01); *H01L 51/441* (2013.01)

(58) Field of Classification Search
CPC ................ C07D 209/52; C01B 32/154; H01L 31/02167; H01L 51/0047; H01L 51/4253; H01L 51/441
See application file for complete search history.

(56) References Cited

U.S. PATENT DOCUMENTS

| | | | | |
|---|---|---|---|---|
| 2010/0127244 | A1* | 5/2010 | Kronholm | H01L 51/0047 257/40 |
| 2011/0001093 | A1 | 1/2011 | Itoh et al. | |
| 2011/0193073 | A1 | 8/2011 | Itoh et al. | |
| 2012/0211082 | A1* | 8/2012 | Akiyama | C07F 9/5325 136/263 |
| 2015/0158814 | A1 | 6/2015 | Yanagawa et al. | |
| 2016/0093807 | A1 | 3/2016 | Nagai et al. | |
| 2016/0126462 | A1 | 5/2016 | Nagai et al. | |

FOREIGN PATENT DOCUMENTS

| | | |
|---|---|---|
| EP | 2 905 277 | 8/2015 |
| JP | 2009-84264 | 4/2009 |
| JP | 2010-92964 | 4/2010 |
| JP | 2011-119648 | 6/2011 |
| JP | 2011-140480 | 7/2011 |
| JP | 2011-181719 | 9/2011 |
| JP | 2012-89538 | 5/2012 |
| JP | 2015-13844 | * 1/2015 |

(Continued)

OTHER PUBLICATIONS

Machine translated document (Year: 2015).*
International Search Report dated Jan. 10, 2017 in International (PCT) Application No. PCT/JP2016/079795.
Matsumoto et al., "Design of fulleropyrrolidine derivatives as an acceptor molecule in a thin layer organic solar cell", Journal of Materials Chemistry, vol. 20, 2010, pp. 9226-9230.
Karakawa et al., "N-phenyl[60]fulleropyrrolidines: alternative acceptor materials to $PC_{61}BM$ for high performance organic photovoltaic cells", J. Mater. Chem. A, vol. 2, 2014, pp. 20889-20895.

(Continued)

*Primary Examiner* — Ahmed N Sefer
(74) *Attorney, Agent, or Firm* — Wenderoth, Lind & Ponack, L.L.P.

(57) ABSTRACT

An object of the present invention is to provide a novel fullerene derivative usable in n-type semiconductor materials for organic thin-film solar cells and the like. The object is achieved by a fullerene derivative represented by formula (1)

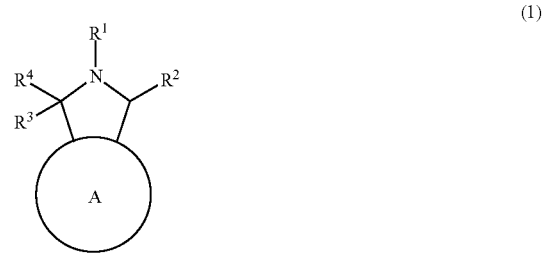

(1)

wherein $R^1$ represents aryl optionally substituted with at least one substituent, $R^2$ represents an organic group, $R^3$ represents an organic group, with the proviso that at least one of $R^2$ and $R^3$ is alkyl optionally substituted with at least one substituent or alkyl ether optionally substituted with at least one substituent, $R^4$ represents hydrogen or an organic group, and a ring A represents a fullerene ring.

11 Claims, No Drawings

(56) References Cited

FOREIGN PATENT DOCUMENTS

| WO | 2012/090971 | 7/2012 |
| WO | 2014/185535 | 11/2014 |
| WO | 2014/185536 | 11/2014 |

OTHER PUBLICATIONS

Extended European Search Report dated Apr. 10, 2019 in corresponding European Patent Application No. 16853695.1.

* cited by examiner

FULLERENE DERIVATIVE AND N-TYPE SEMICONDUCTOR MATERIAL

TECHNICAL FIELD

The present invention relates to a fullerene derivative, an n-type semiconductor material, and the like.

BACKGROUND ART

Organic thin-film solar cells are formed by a coating technique using a solution of an organic compound, which is a photoelectric conversion material. The cells have various advantages: for example, 1) device production costs are low; 2) area expansion is easy; 3) the cells are more flexible than inorganic materials, such as silicon, thus enabling a wider range of applications; and 4) resource depletion is less likely. Thus, recent years have seen the development of organic thin-film solar cells, and in particular, the use of the bulk heterojunction structure has led to a significant increase in conversion, efficiency, attracting widespread attention.

Of the photoelectric conversion basic materials used for organic thin-film solar cells, poly-3-hexylthiophene (P3HT) is in particular known as an organic p-type semiconductor material exhibiting excellent performance. With an aim to obtain advanced materials, recent developments have provided compounds (donor-acceptor-type π-conjugated polymers) that can absorb broad wavelengths of solar light or that have their energy levels tuned, leading to significant improvements in performance. Examples of such compounds include poly-p-phenylenevinylene and poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7).

Regarding n-type semiconductors as well, fullerene derivatives have been intensively studied, and [6,6]-phenyl-$C_{61}$-butyric acid methyl ester (PCBM) has been reported as a material having excellent photoelectric conversion performance (see, e.g., Patent Literature 1 and 2 listed below). Nonetheless, there have been few reports that demonstrate stable and excellent conversion efficiency of fullerene derivatives except for PCBM.

PCBM is a fullerene derivative having a 3-membered ring moiety, and most of the fullerene derivatives so far reported also contain a 3-membered ring moiety as with PCBM.

Regarding fullerene derivatives other than fullerene derivatives having a 3-membered ring moiety, fullerene derivatives having a 5-membered ring moiety are also known; however, there are few reports of them. Non-patent Literature 1 discloses a fullerene derivative having a pyrrolidine ring that has substituents only at positions 1 and 2. Patent Literature 3 teaches that among the fullerene derivatives having a pyrrolidine ring substituted only at positions 1 and 2, in particular, the use of fullerene derivatives having substituted or unsubstituted phenyl at position 1 in n-type semiconductors for solar cells can achieve high conversion efficiency. Patent Literature 4 discloses a fullerene derivative having a pyrrolidine ring substituted only at positions 1 and 2. Patent Literature 5 discloses a fullerene derivative having two or more pyrrolidine rings. Non-patent Literature 2 teaches that it is effective to use a fullerene derivative having a pyrrolidine ring substituted with phenyl at position 1 in n-type semiconductors for organic thin-film solar cells.

CITATION LIST

Patent Literature

Patent Literature 1: JP2009-84264A
Patent Literature 2: JP2010-92964A
Patent Literature 3: JP2012-089538A
Patent Literature 4: WO2014/185536
Patent Literature 5: JP2011-181719A Non-Patent Literature Non-patent Literature 1: T. Itoh et al., Journal of Materials Chemistry, 2010, vol. 20, p. 9226
Non-patent Literature 2: M. Karakawa et al., Journal of Material Chemistry A, 2014, vol. 2, p. 20889

SUMMARY OF INVENTION

Technical Problem

A device using the fullerene derivative disclosed in Non-patent Literature 1 achieves higher conversion efficiency than devices using PCBM. However, this comparison was made between special devices from which a current collector material of the positive electrode (ITO electrode) was removed.

As noted above, development of practicable organic thin-film solar cells using a fullerene derivative remains to be seen, and there has still been demand for the development of a novel fullerene derivative usable in n-type semiconductor materials for organic thin-film solar cells and the like.

A major object of the present invention is to provide a material that exhibits excellent performance as an n-type semiconductor, in particular, an n-type semiconductor for photoelectric conversion elements, such as organic thin-film solar cells.

An example of typically listed excellent performance of an n-type semiconductor for photoelectric conversion elements, such as organic thin-film solar cells is high conversion efficiency.

Thus, an object of the present invention is to provide a novel fullerene derivative that achieves high conversion efficiency.

Typically, to activate an electrical device, a predetermined drive voltage or a higher voltage is required. Thus, when the output voltage of one cell for a solar battery is low, many cells are required. If an n-type semiconductor that can generate a high voltage is provided, fewer cells are required, reducing the space for the solar battery.

A feature of organic thin-film solar cells is that the cells make it possible to prepare devices with a large area at low cost by using a solution coating technique in the production process of solar batteries. Thus, the solubility of a material used is a performance that plays an important role in this technique.

Specifically, there has been demand for materials having a suitable solubility that makes it possible to use solution coating in device production and that exhibit high electric generation efficiency.

Thus, an object of the present invention is to provide a novel fullerene derivative that simplifies the production of a device and that enables high voltage output.

Thus, an object of the present invention is to provide a fullerene derivative that exhibits high conversion efficiency and that enables high voltage output.

Solution to Problem

The present inventors found that the problems can be solved by the fullerene derivative represented by formula (1) described below.

The present invention includes the following subject matter.

Item 1.

A fullerene derivative represented by formula (1)

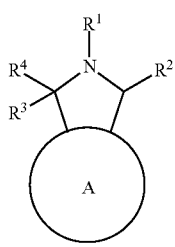

wherein $R^1$ represents aryl optionally substituted with at least one substituent, $R^2$ represents an organic group, $R^3$ represents an organic group, with the proviso that at least one of $R^2$ and $R^3$ is alkyl optionally substituted with at least one substituent or alkyl ether optionally substituted with at least one substituent, $R^4$ represents a hydrogen atom or an organic group, and ring A represents a fullerene ring.

Item 2.

The fullerene derivative according to item 1, wherein $R^1$ is aryl optionally substituted with at least one substituent selected from the group consisting of fluorine, chlorine, bromine, iodine, methyl, methoxy, and cyano.

Item 3.

The fullerene derivative according to item 1 or 2, wherein $R^1$ is phenyl optionally substituted with at least one fluorine atom.

Item 4.

The fullerene derivative according to any one of items 1 to 3, wherein $R^2$ is alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

Item 5.

The fullerene derivative according to any one of items 1 to 4, wherein $R^3$ and $R^4$ are identical or different and each represent hydrogen, alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

Item 6.

The fullerene derivative according to any one of items 1 to 5, wherein ring A is a $C_{60}$ fullerene or a $C_{70}$ fullerene.

Item 7.

A fullerene derivative that has an LUMO level of −3.65 eV or more (1), and that has a solubility in toluene at room temperature of 0.5% or more (2).

Item 8.

An n-type semiconductor material comprising the fullerene derivative according to any one of items 1 to 7.

Item 9.

The n-type semiconductor material according to item 8, which is for use in an organic thin-film solar cell.

Item 10.

An organic power-generating layer comprising the n-type semiconductor material according to item 9.

Item 11.

A photoelectric conversion element comprising the organic power-generating layer according to item 10.

Item 12.

The photoelectric conversion element according to item 11, which is an organic thin-film solar cell.

Advantageous Effects of Invention

The present invention provides a fullerene derivative that exhibits high conversion efficiency, and that enables high voltage output.

In an embodiment of the present invention, a fullerene derivative that exhibits a high solubility in an organic solvent is provided.

DESCRIPTION OF EMBODIMENTS

Terms

As used herein, unless particularly specified otherwise, the term "organic group" refers to a group containing at least one carbon atom as its constituent atom.

As used herein, unless particularly specified otherwise, examples of "organic group" include hydrocarbon groups.

As used herein, unless particularly specified otherwise, the term "hydrocarbon group" refers to a group containing at least one carbon atom and at least one hydrogen atom as its constituent atoms.

As used herein, the team "hydrocarbon group" may be referred to as "hydrocarbyl group."

As used herein, unless particularly specified otherwise, examples of "hydrocarbon group" include aliphatic hydrocarbon groups optionally substituted with at least one aromatic hydrocarbon group (e.g., benzyl group) and aromatic hydrocarbon groups (aryl group) optionally substituted with at least one aliphatic hydrocarbon group.

As used herein, unless particularly specified otherwise, the term "aliphatic hydrocarbon group" may be a linear, branched, or cyclic aliphatic hydrocarbon group, or a combination thereof.

As used herein, unless particularly specified otherwise, the term "aliphatic hydrocarbon group" may be a saturated or unsaturated aliphatic hydrocarbon group.

As used herein, unless particularly specified otherwise, examples of "aliphatic hydrocarbon group" includes alkyl, alkenyl, alkynyl, and cycloalkyl.

As used herein, unless particularly specified otherwise, the team "alkyl" refers to a linear or branched $C_{1-10}$ alkyl, such as methyl, ethyl, propyl, isopropyl, butyl, isobutyl, sec-butyl, tert-butyl, pentyl, isopentyl, neopentyl, and hexyl.

As used herein, unless particularly specified otherwise, the term "alkenyl" refers to a linear or branched $C_{1-10}$ alkenyl, such as vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

As used herein, unless particularly specified otherwise, the term "alkynyl" refers to a linear or branched $C_{2-6}$ alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein, unless particularly specified otherwise, the term "cycloalkyl" refers to $C_{3-8}$ cycloalkyl, such as cyclopentyl, cyclohexyl, and cycloheptyl.

As used herein, unless particularly specified otherwise, the term "aromatic hydrocarbon group (aryl group)" refers to phenyl, naphthyl, phenanthryl, anthryl, and pyrenyl.

As used herein, unless particularly specified otherwise, the term "alkoxy" refers to, for example, a group represented by RO— (wherein R represents alkyl).

As used herein, unless particularly specified otherwise, the term "ester" refers to an organic group having an ester bond (i.e., —C(=O)—O— or —O—C(=O)—). Examples of ester include groups represented by formula $RCO_2$— (wherein R represents alkyl) and groups represented by formula $R^a$—$CO_2$—$R^b$— (wherein $R^a$ represents alkyl and $R^b$ represents alkylene).

As used herein, unless particularly specified otherwise, the term "ether" refers to a group having an ether bond (—O—).

Examples of ether include polyether. Examples of polyether include groups represented by formula $R^a$—(O—$R^b$)$_n$— (wherein $R^a$ represents alkyl; $R^b$, in each occurrence, is identical or different and represents alkylene; and n is an integer of 1 or more). Alkylene is a divalent group formed by removing one hydrogen atom from an alkyl group.

Examples of ether also include hydrocarbyl ether groups. A hydrocarbyl ether group refers to a hydrocarbon group having at least one ether bond. A hydrocarbyl group having at least one ether bond may be a hydrocarbyl group into which at least one ether bond is inserted. Examples include a benzyl oxy group.

Examples of the hydrocarbon group having at least one ether bond include alkyl having at least one ether bond. Alkyl having at least one ether bond may be alkyl into which at least one ether bond is inserted. As used herein, such a group may be referred to as an "alkyl ether group."

As used herein, unless particularly specified otherwise, the ter "acyl" includes alkanoyl. As used herein, unless particularly specified otherwise, the term "alkanoyl" refers to, for example, a group represented by RCO— (wherein R represents alkyl).

As used herein, a "5-membered heteroaryl group" refers to, for example, a 5-membered heteroaryl group containing as members of its ring at least one heteroatom (e.g., 1, 2, or 3 heteroatoms) selected from the group consisting of oxygen, sulfur, and nitrogen, unless indicated otherwise; examples of the 5-membered heteroaryl group include pyrrolyl (e.g., 1-pyrrolyl, 2-pyrrolyl, and 3-pyrrolyl), furyl (e.g., 2-furyl, and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), and thiadiazolyl (e.g., 1,2,4-thiadiazol-3-yl and 1,2,4-thiadiazol-5-yl).

The following describes in detail a fullerene derivative of the present invention, an n-type semiconductor material comprising the fullerene derivative, and the like.

Fullerene Derivative

The fullerene derivative of the present invention is represented by the following formula (1)

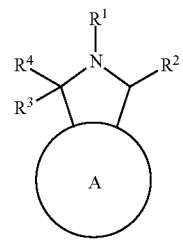

(1)

wherein
$R^1$ represents aryl optionally substituted with at least one substituent,
$R^2$ represents an organic group,
$R^3$ represents an organic group, with the proviso that at least one of $R^2$ and $R^3$ is alkyl optionally substituted with at least one substituent or alkyl ether optionally substituted with at least one substituent,
$R^4$ represents an hydrogen atom or an organic group, and ring A represents a fullerene ring.

As usually understood by a person skilled in the art, $R^1$ does not form a ring with $R^2$, $R^3$, or $R^4$.

Examples of the substituent in the "aryl optionally substituted with at least one substituent" represented by $R^1$ include fluorine, chlorine, bromine, iodine, alkyl optionally substituted with at least one fluorine atom (preferably methyl), alkoxy optionally substituted with at least one fluorine atom (preferably methoxy), ester, and cyano. The number of substituents may be at least one and equal to or lower than the maximum number with which substitution is possible. The preferable number of substituents is, for example, 1 to 4, 1 to 3, 1 to 2, or 1.

The aryl optionally substituted with at least one substituent represented by $R^1$ may be preferably aryl optionally substituted with at least one substituent selected from the group consisting of fluorine, chlorine, bromine, iodine, methyl, methoxy, and cyano.

The aryl optionally substituted with at least one substituent represented by $R^1$ may be preferably unsubstituted aryl.

The aryl in "aryl optionally substituted with at least one substituent" represented by $R^1$ may be preferably phenyl.

$R^1$ may be preferably a group represented by the following partial structural formula

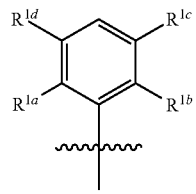

wherein
$R^{1a}$ and $R^{1b}$ are identical or different and represent hydrogen or fluorine, and
$R^{1c}$ and $R^{1d}$ are identical or different and represent hydrogen, fluorine, alkyl optionally substituted with at least one fluorine atom, alkoxy optionally substituted with at least one fluorine atom, ester, or cyano.

Because of such a substituent attached to the nitrogen atom that is a constituent atom of the pyrrolidine site of formula (1), the fullerene derivative of the present invention exhibits decreased properties as a base due to the nitrogen atom, thereby having excellent properties as an n-type semiconductor material.

Because of a compact, substituted or unsubstituted phenyl group (i.e., phenyl, 2-fluorophenyl, or 2,6-difluorophenyl) represented by the following partial structural formula

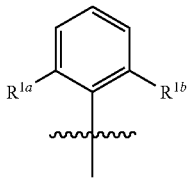

attached to the nitrogen atom that is a constituent atom of the pyrrolidine site of formula (1), the fullerene derivative in this embodiment exhibits decreased properties as a base due to the nitrogen atom, thereby having excellent properties as an n-type semiconductor material.

In this embodiment, $R^1$ preferably represents phenyl substituted with 1 or 2 fluorine atoms, or a 5-membered heteroaryl group optionally substituted with 1 to 3 methyl groups.

Because $R^1$ is such a compact, substituted or unsubstituted aromatic group, the fullerene derivative of the present invention exhibits excellent properties as an n-type semiconductor material.

In this embodiment, "phenyl substituted with 1 or 2 fluorine atoms" represented by $R^1$ is preferably a phenyl group substituted with 1 or 2 fluorine atoms at its ortho-position (i.e., 2-fluorophenyl or 2,6-difluorophenyl).

In this embodiment, $R^1$ is preferably, for example, phenyl, 2-fluorophenyl, 2-cyanophenyl, 2,6-methoxyphenyl, 2,6-dichlorophenyl, 2,6-difluorophenyl, 2,6-dimethylphenyl, 2,6-cyanophenyl, 2-methoxyphenyl, 2-chlorophenyl, 2-methylphenyl, 2-thienyl, or 2-thiazolyl, more preferably, for example, phenyl, 2-fluorophenyl, 2,6-difluorophenyl, 2-thienyl, or 2-thiazolyl, and more preferably, for example, phenyl, 2-fluorophenyl, or 2,6-difluorophenyl.

A preferable embodiment of the fullerene derivative represented by formula (1) is a fullerene derivative wherein at least one of $R^{1a}$ or $R^{1b}$ is a fluorine atom.

Another preferable embodiment of the fullerene derivative represented by formula (1) is a fullerene derivative wherein both $R^{1a}$ and $R^{1b}$ are a hydrogen atom; and $R^1$ represents phenyl substituted with 1 or 2 fluorine atoms or a 5-membered heteroaryl group substituted with 1 to 3 methyl groups.

$R^1$ is more preferably, for example, phenyl, 2-fluorophenyl or 2,6-difluorophenyl, and still more preferably, for example, phenyl.

$R^2$ is preferably alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

Examples of the substituent and the number of substituents in "alkyl optionally substituted with at least one substituent," "alkenyl optionally substituted with at least one substituent," "alkynyl optionally substituted with at least one substituent," "aryl optionally substituted with at least one substituent," "ether optionally substituted with at least one substituent," and "ester optionally substituted with at least one substituent" all represented by $R^2$ are those described in the examples of substituents and the number of substituents for "aryl optionally substituted with at least one substituent" represented by $R^1$.

$R^2$ is more preferably
(1) alkyl having 2 to 18 carbon atoms (preferably 3 to 12, more preferably 4 to 10, still more preferably 5 to 8 carbon atoms),
(2) aryl optionally substituted with at least one substituent selected from fluorine, alkyl optionally substituted with at least one fluorine atom, alkoxy optionally substituted with at least one fluorine atom, ester, and cyano (preferably phenyl),
(3) ether having 1 to 12 carbon atoms (preferably 1 to 10, more preferably 1 to 8, and still more preferably 1 to 6 carbon atoms) (preferably, alkyl ether), or
(4) ester having 2 to 12 carbon atoms (preferably 2 to 10, more preferably 2 to 8, and still more preferably 2 to 6 carbon atoms).

In another embodiment of the present invention, $R^2$ is still more preferably alkyl having 2 to 18 carbon atoms (preferably 3 to 12, more preferably 4 to 10, and still more preferably 5 to 8 carbon atoms), phenyl optionally substituted with at least one substituent selected from fluorine, alkyl optionally substituted with at least one fluorine atom, alkoxy optionally substituted with at least one fluorine atom, ester, and cyano, or ether having 1 to 12 carbon atoms (preferably 1 to 10, more preferably 1 to 8, and still more preferably 1 to 6 carbon atoms) (preferably alkyl ether).

$R^2$ is still more preferably alkyl having 5 to 8 carbon atoms or aryl.

In a preferable embodiment of the present invention, $R^2$ is
[1] a $C_{2-8}$ alkyl group
[examples: (a) linear $C_{2-8}$ alkyl (e.g., ethyl, n-propyl, n-butyl, n-pentyl, n-hexyl, n-heptyl, and n-octyl); and
(b) branched alkyl (e.g., isopropyl, isobutyl, sec-butyl, isopentyl, 1-methylpentyl, 2-methylpentyl, 3-methylpentyl, 4-methylpentyl, 1-ethylbutyl, 2-ethylbutyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1-(1-methylethyl)butyl, 1-(1-methylethyl)-2-methylpropyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-n-propylpentyl, 2-propylpentyl, 1-(1-methylethyl) pentyl, 1-butylbutyl, 1-butyl-2-methylbutyl, 1-butyl-3-methylbutyl, 1-(1,1-dimethylethyl)butylbutyl, tert-butyl, 1,1-dimethylpropyl, 1,1-dimethylbutyl, 1,2-dimethylbutyl, 1,3-dimethylbutyl, 2,3-dimethylbutyl, 1-ethyl-2-methylpropyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethyl-1-methylbutyl, 1-ethyl-2-methylbutyl, 1-ethyl-3-methylbutyl, 2-ethyl-1-methylbutyl, 2-ethyl-3-methylbutyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 1-ethyl-2-methylpentyl, 1-ethyl-3-methylpentyl, 1-ethyl-4-methylpentyl, 2-ethyl-1-methylpentyl, 2-ethyl-2- methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1-propyl-1-methylbutyl, 1-propyl-2-methylbutyl, 1-propyl-3-methylbutyl, 1-(1-methylethyl)-1-methylbutyl, 1-(1-methylethyl)-2-methylbutyl, 1-(1-methylethyl)-3-methylbutyl, 1,1-diethylbutyl, and 1,2-diethylbutyl)];

[2] a $C_{1-8}$ alkyloxy group

[examples: (a) linear $C_{1-8}$ alkyloxy (e.g., methyloxy, ethyloxy, n-propyloxy, n-butyloxy, n-pentyloxy, n-hexyloxy, n-heptyloxy, and n-octyloxy); and (b) branched $C_{3-8}$ alkyloxy (e.g., isopropyloxy, isobutyloxy, sec-butyloxy, isopentyloxy, 1-methylpentyloxy, 2-methylpentyloxy, 3-methylpentyloxy, 4-methylpentyloxy, 1-ethylbutyloxy, 2-ethylbutyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylbutyloxy, 1-(1-methylethyl)butyloxy, 1-(1-methylethyl)-2-methylpropyloxy, 1-methylheptyloxy, 2-methylheptyloxy, 3-methylheptyloxy, 4-methylheptyloxy, 5-methylheptyloxy, 6-methylheptyloxy, 1-ethylhexyloxy, 2-ethylhexyloxy, 3-ethylhexyloxy, 4-ethylhexyloxy, 1-n-propylpentyloxy, 2-propylpentyloxy, 1-(1-methylethyl)pentyloxy, 1-butylbutyloxy, 1-butyl-2-methylbutyloxy, 1-butyl-3-methylbutyloxy, 1-(1,1-dimethylethyl)butylbutyloxy, tert-butyloxy, 1,1-dimethylpropyloxy, 1,1-dimethylbutyloxy, 1,2-dimethylbutyloxy, 1,3-dimethylbutyloxy, 2,3-dimethylbutyloxy, 1-ethyl-2-methylpropyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 1-ethyl-1-methylbutyloxy, 1-ethyl-2-methylbutyloxy, 1-ethyl-3-methylbutyloxy, 2-ethyl-1-methylbutyloxy, 2-ethyl-3-methylbutyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-dimethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 1-ethyl-2-methylpentyloxy, 1-ethyl-3-methylpentyloxy, 1-ethyl-4-methylpentyloxy, 2-ethyl-1-methylpentyloxy, 2-ethyl-2-methylpentyloxy, 2-ethyl-3-methylpentyloxy, 2-ethyl-4-methylpentyloxy, 3-ethyl-1-methylpentyloxy, 3-ethyl-2-methylpentyloxy, 3-ethyl-3-methylpentyloxy, 3-ethyl-4-methylpentyloxy, 1-propyl-1-methylbutyloxy, 1-propyl-2-methylbutyloxy, 1-propyl-3-methylbutyloxy, 1-(1-methylethyl)-1-methylbutyloxy, 1-(1-methylethyl)-2-methylbutyloxy, 1-(1-methylethyl)-3-methylbutyloxy, 1,1-diethylbutyloxy, and 1,2-diethylbutyloxy)]

[3] a $C_{1-8}$ alkyl-carbonyloxy group;

[examples: (a) linear $C_{1-8}$ alkyl-carbonyloxy (e.g., methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, and n-octylcarbonyloxy); and (b) branched $C_{3-8}$ alkyl-carbonyloxy (e.g., isopropyl carbonyloxy, isobutyl carbonyloxy, sec-butyl carbonyloxy, isopentyl carbonyloxy, 1-methylpentyl carbonyloxy, 2-methylpentyl carbonyloxy, 3-methylpentyl carbonyloxy, 4-methylpentyl carbonyloxy, 1-ethylbutyl carbonyloxy, 2-ethylbutyl carbonyloxy, 1-methylhexyl carbonyloxy, 2-methylhexyl carbonyloxy, 3-methylhexyl carbonyloxy, 4-methylhexyl carbonyloxy, 5-methylhexyl carbonyloxy, 1-ethylpentyl carbonyloxy, 2-ethylpentyl carbonyloxy, 3-ethylpentyl carbonyloxy, 1-propylbutyl carbonyloxy, 1-(1-methylethyl)butyl carbonyloxy, 1-(1-methylethyl)-2-methylpropyl carbonyloxy, 1-methylheptyl carbonyloxy, 2-methylheptyl carbonyloxy, 3-methylheptyl carbonyloxy, 4-methylheptyl carbonyloxy, 5-methylheptyl carbonyloxy, 6-methylheptyl carbonyloxy, 1-ethylhexyl carbonyloxy, 2-ethylhexyl carbonyloxy, 3-ethylhexyl carbonyloxy, 4-ethylhexyl carbonyloxy, 1-n-propylpentyl carbonyloxy, 2-propylpentyl carbonyloxy, 1-(1-methylethyl)pentyl carbonyloxy, 1-butylbutyl carbonyloxy, 1-butyl-2-methylbutyl carbonyloxy, 1-butyl-3-methylbutyl carbonyloxy, 1-(1,1-dimethylethyl)butylbutyl carbonyloxy, tert-butyl carbonyloxy, 1,1-dimethylpropyl carbonyloxy, 1,1-dimethylbutyl carbonyloxy, 1,2-dimethylbutyl carbonyloxy, 1,3-dimethylbutyl carbonyloxy, 2,3-dimethylbutyl carbonyloxy, 1-ethyl-2-methylpropyl carbonyloxy, 1,1-dimethylpentyl carbonyloxy, 1,2-dimethylpentyl carbonyloxy, 1,3-dimethylpentyl carbonyloxy, 1,4-dimethylpentyl carbonyloxy, 2,2-dimethylpentyl carbonyloxy, 2,3-dimethylpentyl carbonyloxy, 2,4-dimethylpentyl carbonyloxy, 3,3-dimethylpentyl carbonyloxy, 3,4-dimethylpentyl carbonyloxy, 1-ethyl-1-methylbutyl carbonyloxy, 1-ethyl-2-methylbutyl carbonyloxy, 1-ethyl-3-methylbutyl carbonyloxy, 2-ethyl-1-methylbutyl carbonyloxy, 2-ethyl-3-methylbutyl carbonyloxy, 1,1-dimethylhexyl carbonyloxy, 1,2-dimethylhexyl carbonyloxy, 1,3-dimethylhexyl carbonyloxy, 1,4-dimethylhexyl carbonyloxy, 1,5-dimethylhexyl carbonyloxy, 2,2-dimethylhexyl carbonyloxy, 2,3-dimethylhexyl carbonyloxy, 2,4-dimethylhexyl carbonyloxy, 2,5-dimethylhexyl carbonyloxy, 3,3-dimethylhexyl carbonyloxy, 3,4-dimethylhexyl carbonyloxy, 3,5-dimethylhexyl carbonyloxy, 4,4-dimethylhexyl carbonyloxy, 4,5-dimethylhexyl carbonyloxy, 1-ethyl-2-methylpentyl carbonyloxy, 1-ethyl-3-methylpentyl carbonyloxy, 1-ethyl-4-methylpentyl carbonyloxy, 2-ethyl-1-methylpentyl carbonyloxy, 2-ethyl-2-methylpentyl carbonyloxy, 2-ethyl-3-methylpentyl carbonyloxy, 2-ethyl-4-methylpentyl carbonyloxy, 3-ethyl-1-methylpentyl carbonyloxy, 3-ethyl-2-methylpentyl carbonyloxy, 3-ethyl-3-methylpentyl carbonyloxy, 3-ethyl-4-methylpentyl carbonyloxy, 1-propyl-1-methylbutyl carbonyloxy, 1-propyl-2-methylbutyl carbonyloxy, 1-propyl-3-methylbutyl carbonyloxy, 1-(1-methylethyl)-1-methylbutyl carbonyloxy, 1-(1-methylethyl)-2-methylbutyl carbonyloxy, 1-(1-methylethyl)-3-methylbutyl carbonyloxy, 1,1-diethylbutyl carbonyloxy, and 1,2-diethylbutyl carbonyloxy)]

[4] a $C_{1-8}$ alkyl-oxycarbonyl group

[examples: (a) linear $C_{1-8}$ alkyl-oxycarbonyl (e.g., methyloxycarbonyl, ethyloxycarbonyl, n-propyloxycarbonyl, n-butyloxycarbonyl, n-pentyloxycarbonyl, n-hexyloxycarbonyl, n-heptyloxycarbonyl, and n-octyloxycarbonyl); and (b) branched $0_{3-8}$ alkyl-oxycarbonyl (e.g., isopropyl oxycarbonyl, isobutyl oxycarbonyl, sec-butyl oxycarbonyl, isopentyl oxycarbonyl, 1-methylpentyl oxycarbonyl, 2-methylpentyl oxycarbonyl, 3-methylpentyl oxycarbonyl, 4-methylpentyl oxycarbonyl, 1-ethylbutyl oxycarbonyl, 2-ethylbutyl oxycarbonyl, 1-methylhexyl oxycarbonyl, 2-methylhexyl oxycarbonyl, 3-methylhexyl oxycarbonyl, 4-methylhexyl oxycarbonyl, 5-methylhexyl oxycarbonyl, 1-ethylpentyl oxycarbonyl, 2-ethylpentyl oxycarbonyl, 3-ethylpentyl oxycarbonyl, 1-propylbutyl oxycarbonyl, 1-(1-methylethyl) butyl oxycarbonyl, 1-(1-methylethyl)-2-methylpropyl oxycarbonyl, 1-methylheptyl oxycarbonyl, 2-methylheptyl oxycarbonyl, 3-methylheptyl oxycarbonyl, 4-methylheptyl oxycarbonyl, 5-methylheptyl oxycarbonyl, 6-methylheptyl oxycarbonyl, 1-ethylhexyl oxycarbonyl, 2-ethylhexyl oxycarbonyl, 3-ethylhexyl oxycarbonyl, 4-ethylhexyl oxycarbonyl, 1-n-propylpentyl oxycarbonyl, 2-propylpentyl oxycarbonyl, 1-(1-methylethyl)pentyl oxycarbonyl, 1-butylbutyl oxycarbonyl, 1-butyl-2-methylbutyl oxycarbonyl, 1-butyl-3-methylbutyl oxycarbonyl, 1-(1,1-dimethylethyl)butylbutyl oxycarbonyl, tert-butyl oxycarbonyl, 1,1-dimethylpropyl oxycarbonyl, 1,1-dimethylbutyl oxycarbonyl, 1,2-dimethylbutyl oxycarbonyl, 1,3-dimethylbutyl oxycarbonyl, 2,3-dimethylbutyl oxycarbonyl, 1-ethyl-2-methylpropyl oxycarbonyl, 1,1-dimethylpentyl oxycarbonyl, 1,2-dimethylpentyl oxycarbonyl, 1,3-dimethylpentyl oxycarbonyl, 1,4-dimethylpentyl oxycarbonyl, 2,2-dimethylpentyl oxycarbonyl, 2,3-dimethylpentyl oxycarbonyl, 2,4-dimethylpentyl oxycarbonyl, 3,3-dimethylpentyl oxycarbonyl, 3,4-dimethylpentyl oxycarbonyl, 1-ethyl-1-methylbutyl oxycarbonyl, 1-ethyl-2-methylbutyl oxycarbonyl, 1-ethyl-3-methylbutyl oxycarbonyl, 2-ethyl-1-methylbutyl oxycarbonyl, 2-ethyl-3-methylbutyl oxycarbonyl, 1,1-dimethylhexyl oxycarbonyl, 1,2-dimethylhexyl oxycarbonyl, 1,3-dimethylhexyl oxycarbonyl, 1,4-dimethylhexyl oxycarbonyl, 1,5-dimethylhexyl oxycarbonyl, 2,2-dimethylhexyl oxycarbonyl, 2,3-dimethylhexyl oxycarbonyl, 2,4-dimethylhexyl oxycarbonyl, 2,5-dimethylhexyl oxycarbonyl, 3,3-dimethylhexyl oxycarbonyl, 3,4-dimethylhexyl oxycarbonyl, 3,5-dimethylhexyl oxycarbonyl, 4,4-dimethylhexyl oxycarbonyl, 4,5-dimethylhexyl oxycarbonyl, 1-ethyl-2-methylpentyl oxycarbonyl, 1-ethyl-3-methylpentyl oxycarbonyl, 1-ethyl-4-methylpentyl oxycarbonyl, 2-ethyl-1-methylpentyl oxycarbonyl, 2-ethyl-2-methylpentyl oxycarbonyl, 2-ethyl-3-methylpentyl oxycarbonyl, 2-ethyl-4-methylpentyl oxycarbonyl, 3-ethyl-1-methylpentyl oxycarbonyl, 3-ethyl-2-methylpentyl oxycarbonyl, 3-ethyl-3-methylpentyl oxycarbonyl, 3-ethyl-4-methylpentyl oxycarbonyl, 1-propyl-1-methylbutyl oxycarbonyl, 1-propyl-2-methylbutyl oxycarbonyl, 1-propyl-3-methylbutyl oxycarbonyl, 1-(1-methylethyl)-1-methylbutyl oxycarbonyl, 1-(1-methylethyl)-2-methylbutyl oxycarbonyl, 1-(1-methylethyl)-3-methylbutyl oxycarbonyl, 1,1-diethylbutyl oxycarbonyl, and 1,2-diethylbutyl oxycarbonyl)];

[5] a $C_{1-8}$ ether group

[examples: (1) a group formed by introducing at least one (e.g., 1, 2, 3, or 4) ether oxygen into alkyl listed in [1] above or (2) a $C_{1-8}$ ether group represented by each of the following formulas:

H—$C_pH_{2p}$—O—$C_qH_{2q}$— wherein p is 1 to 7, q is 1 to 7, and p+q is 2 to 8; H—$C_pH_{2p}$—O—$C_qH_{2q}$—O—$C_rH_{2r}$— wherein p is 1 to 6, q is 1 to 6, r is 1 to 6 and p+q+r is 3 to 8; or H—$C_pH_{2p}$—O—$C_qH_{2q}$—O—$C_rH_{2r}$—O—$C_sH_{2s}$— wherein p is 1 to 6, q is 1 to 6, r is 1 to 6, and p+q+r+s is 4 to 8 (in these formulas, the alkylene chains represented by $C_pH_{2p}$, $C_qH_{2q}$, $C_rH_{2r}$, or $C_sH_{2s}$ may be independently a linear or branched chain)]; or

[6] a phenyl group, a naphthyl group, or a pyrenyl group each optionally substituted with at least one substituent selected from the group consisting of fluorine, methyl, groups listed in [1] to [5], and cyano.

$R^2$ is still more preferably hexyl, 2-ethylhexyl, phenyl, or pyrenyl.

In particular, when $R^2$ is alkyl, the fullerene derivative of the present invention can further exhibit high solubility in an organic solvent. Examples of the organic solvent include carbon disulfide, chloroform, dichloroethane, toluene, xylene, chlorobenzene, and dichlorobenzene. Thus, when the fullerene derivative of the present invention is used in, for example, an n-type semiconductor for photoelectric conversion elements, such as organic thin-film solar cells, the fullerene derivative suitably dissolves in an organic solvent in the production of such a semiconductor; as a result, operability in preparing a device through a coating process is improved, and the n-type semiconductor as a material can suitably be arranged in the obtained device, making it possible to produce an organic thin-film solar cell that exhibits excellent performance.

$R^3$ is preferably alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

Examples of the substituent and the number of substituents in "alkyl optionally substituted with at least one substituent," "alkenyl optionally substituted with at least one substituent," "alkynyl optionally substituted with at least one substituent," "aryl optionally substituted with at least one substituent," "ether optionally substituted with at least one substituent," and "ester optionally substituted with at least one substituent" all represented by $R^3$ are those described the examples of substituents and the number of substituents for "aryl optionally substituted with at least one substituent" represented by $R^1$.

$R^3$ is more preferably alkyl having 2 to 18 carbon atoms (preferably 3 to 12, more preferably 4 to 10, and still more preferably 5 to 8 carbon atoms), ether having 1 to 12 carbon atoms (preferably 1 to 10, more preferably 1 to 8, and still more preferably 1 to 6 carbon atoms), or ester having 2 to 12 carbon atoms (preferably 2 to 10, more preferably 2 to 8, and still more preferably 2 to 6 carbon atoms).

$R^3$ is still more preferably alkyl having 1 to 8 carbon atoms or ether having 5 to 6 carbon atoms.

In a preferable embodiment of the present invention, $R^3$ is

[1] a $C_{1-8}$ alkyl group
(examples include (a) linear $C_{1-8}$ alkyl (e.g., methyl, ethyl, n-propyl, n-butyl, n-pentyl, n-hexyl, n-heptyl, and n-octyl); and (b) branched alkyl (e.g., isopropyl, isobutyl, sec-butyl, isopentyl, 1-methylpentyl, 2-methylpentyl, 3-methylpentyl, 4-methylpentyl, 1-ethylbutyl, 2-ethylbutyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1-(1-methylethyl)butyl, 1-(1-methylethyl)-2-methylpropyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-n-propylpentyl, 2-propylpentyl, 1-(1-methylethyl)pentyl, 1-butylbutyl, 1-butyl-2-methylbutyl, 1-butyl-3-methylbutyl, 1-(1,1-dimethylethyl)butylbutyl, tert-butyl, 1,1-dimethylpropyl, 1,1-dimethylbutyl, 1,2-dimethylbutyl, 1,3-dimethylbutyl, 2,3-dimethylbutyl, 1-ethyl-2-methylpropyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethyl-1-methylbutyl, 1-ethyl-2-methylbutyl, 1-ethyl-3-methylbutyl, 2-ethyl-1-methylbutyl, 2-ethyl-3-methylbutyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 1-ethyl-2-methylpentyl, 1-ethyl-3-methylpentyl, 1-ethyl-4-methylpentyl, 2-ethyl-1-methylpentyl, 2-ethyl-2-methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1-propyl-1-methylbutyl, 1-propyl-2-methylbutyl, 1-propyl-3-methylbutyl, 1-(1-methylethyl)-1-methylbutyl, 1-(1-methylethyl)-2-methylbutyl, 1-(1-methylethyl)-3-methylbutyl, 1,1-diethylbutyl, and 1,2-diethylbutyl));

[2] a $C_{1-8}$ alkyloxy group
(examples include (a) linear $C_{1-8}$ alkyloxy (e.g., methyloxy, ethyloxy, n-propyloxy, n-butyloxy, n-pentyloxy, n-hexyloxy, n-heptyloxy, and n-octyloxy); and (b) branched $C_{3-8}$ alkyloxy (e.g., isopropyloxy, isobutyloxy, sec-butyloxy, isopentyloxy, 1-methylpentyloxy, 2-methylpentyloxy, 3-methylpentyloxy, 4-methylpentyloxy, 1-ethylbutyloxy, 2-ethylbutyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylbutyloxy, 1-(1-methylethyl)butyloxy, 1-(1-methylethyl)-2-methylpropyloxy, 1-methylheptyloxy, 2-methylheptyloxy, 3-methylheptyloxy, 4-methylheptyloxy, 5-methylheptyloxy, 6-methylheptyloxy, 1-ethylhexyloxy, 2-ethylhexyloxy, 3-ethylhexyloxy, 4-ethylhexyloxy, 1-n-propylpentyloxy, 2-propylpentyloxy, 1-(1-methylethyl)pentyloxy, 1-butylbutyloxy, 1-butyl-2-methylbutyloxy, 1-butyl-3-methylbutyloxy, 1-(1,1-dimethylethyl)butylbutyloxy, tert-butyloxy, 1,1-dimethylpropyloxy, 1,1-dimethylbutyloxy, 1,2-dimethylbutyloxy, 1,3-dimethylbutyloxy, 2,3-dimethylbutyloxy, 1-ethyl-2-methylpropyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 1-ethyl-1-methylbutyloxy, 1-ethyl-2-methylbutyloxy, 1-ethyl-3-methylbutyloxy, 2-ethyl-1-methylbutyloxy, 2-ethyl-3-methylbutyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-dimethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 1-ethyl-2-methylpentyloxy, 1-ethyl-3-methylpentyloxy, 1-ethyl-4-methylpentyloxy, 2-ethyl-1-methylpentyloxy, 2-ethyl-2-methylpentyloxy, 2-ethyl-3-methylpentyloxy, 2-ethyl-4-methylpentyloxy, 3-ethyl-1-methylpentyloxy, 3-ethyl-2-methylpentyloxy, 3-ethyl-3-methylpentyloxy, 3-ethyl-4-methylpentyloxy, 1-propyl-1-methylbutyloxy, 1-propyl-2-methylbutyloxy, 1-propyl-3-methylbutyloxy, 1-(1-methylethyl)-1-methylbutyloxy, 1-(1-methylethyl)-2-methylbutyloxy, 1-(1-methylethyl)-3-methylbutyloxy, 1,1-diethylbutyloxy, and 1,2-diethylbutyloxy))

[3] a $C_{1-8}$ alkyl-carbonyloxy group;
(examples include (a) linear $C_{1-8}$ alkyl-carbonyloxy (e.g., methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, and n-octylcarbonyloxy); and (b) branched $C_{3-8}$ alkyl-carbonyloxy (e.g., isopropyl carbonyloxy, isobutyl carbonyloxy, sec-butyl carbonyloxy, isopentyl carbonyloxy, 1-methylpentyl carbonyloxy, 2-methylpentyl carbonyloxy, 3-methylpentyl carbonyloxy, 4-methylpentyl carbonyloxy, 1-ethylbutyl carbonyloxy, 2-ethylbutyl carbonyloxy, 1-methylhexyl carbonyloxy, 2-methylhexyl carbonyloxy, 3-methylhexyl carbonyloxy, 4-methylhexyl carbonyloxy, 5-methylhexyl carbonyloxy, 1-ethylpentyl carbonyloxy, 2-ethylpentyl carbonyloxy, 3-ethylpentyl carbonyloxy, 1-propylbutyl carbonyloxy, 1-(1-methylethyl)butyl carbonyloxy, 1-(1-methylethyl)-2-methylpropyl carbonyloxy, 1-methylheptyl carbonyloxy, 2-methylheptyl carbonyloxy, 3-methylheptyl carbonyloxy, 4-methylheptyl carbonyloxy, 5-methylheptyl carbonyloxy, 6-methylheptyl carbonyloxy, 1-ethylhexyl carbonyloxy, 2-ethylhexyl carbonyloxy, 3-ethylhexyl carbonyloxy, 4-ethylhexyl carbonyloxy, 1-n-propylpentyl carbonyloxy, 2-propylpentyl carbonyloxy, 1-(1-methylethyl)pentyl carbonyloxy, 1-butylbutyl carbonyloxy, 1-butyl-2-methylbutyl carbonyloxy, 1-butyl-3-methylbutyl carbonyloxy, 1-(1,1-dimethylethyl)butylbutyl carbonyloxy, tert-butyl carbonyloxy, 1,1-dimethylpropyl carbonyloxy, 1,1-dimethylbutyl carbonyloxy, 1,2-dimethylbutyl carbonyloxy, 1,3-dimethylbutyl carbonyloxy, 2,3-dimethylbutyl carbonyloxy, 1-ethyl-2-methylpropyl carbonyloxy, 1,1-dimethylpentyl carbonyloxy, 1,2-dimethylpentyl carbonyloxy, 1,3-dimethylpentyl carbonyloxy, 1,4-dimethylpentyl carbonyloxy, 2,2-dimethylpentyl carbonyloxy, 2,3-dimethylpentyl carbonyloxy, 2,4-dimethylpentyl carbonyloxy, 3,3-dimethylpentyl carbonyloxy, 3,4-dimethylpentyl carbonyloxy, 1-ethyl-1-methylbutyl carbonyloxy, 1-ethyl-2-methylbutyl carbonyloxy, 1-ethyl-3-methylbutyl carbonyloxy, 2-ethyl-1-methylbutyl carbonyloxy, 2-ethyl-3-methylbutyl carbonyloxy, 1,1-dimethylhexyl carbonyloxy, 1,2-dimethylhexyl carbonyloxy, 1,3-dimethylhexyl carbonyloxy, 1,4-dimethylhexyl carbonyloxy, 1,5-dimethylhexyl carbonyloxy, 2,2-dimethylhexyl carbonyloxy, 2,3-dimethylhexyl carbonyloxy, 2,4-dimethylhexyl carbonyloxy, 2,5-dimethylhexyl carbonyloxy, 3,3-dimethylhexyl carbonyloxy, 3,4-dimethylhexyl carbonyloxy, 3,5-dimethylhexyl carbonyloxy, 4,4-dimethylhexyl carbonyloxy, 4,5-dimethylhexyl carbonyloxy, 1-ethyl-2-methylpentyl carbonyloxy, 1-ethyl-3-methylpentyl carbonyloxy, 1-ethyl-4-methylpentyl carbonyloxy, 2-ethyl-1-methylpentyl carbonyloxy, 2-ethyl-2-methylpentyl carbonyloxy, 2-ethyl-3-methylpentyl carbonyloxy, 2-ethyl-4-methylpentyl carbonyloxy, 3-ethyl-1-methylpentyl carbonyloxy, 3-ethyl-2-methylpentyl carbonyloxy, 3-ethyl-3-methylpentyl carbonyloxy, 3-ethyl-4-methylpentyl carbonyloxy, 1-propyl-1-methylbutyl carbonyloxy, 1-propyl-2-methylbutyl carbonyloxy, 1-propyl-3-methylbutyl carbonyloxy, 1-(1-methylethyl)-1-methylbutyl carbonyloxy, 1-(1-methylethyl)-2-methylbutyl carbonyloxy, 1-(1-methylethyl)-3-methylbutyl carbonyloxy, 1,1-diethylbutyl carbonyloxy, and 1,2-diethylbutyl carbonyloxy))

[4] a $C_{1-8}$ alkyl-oxycarbonyl group
(examples include (a) linear $C_{1-8}$ alkyl-oxycarbonyl (e.g., methyloxycarbonyl, ethyloxycarbonyl, n-propyloxycarbonyl, n-butyloxycarbonyl, n-pentyloxycarbonyl, n-hexyloxycarbonyl, n-heptyloxycarbonyl, and n-octyloxycarbonyl); and (b) branched $C_{3-8}$ alkyl-oxycarbonyl (e.g., isopropyl oxycarbonyl, isobutyl oxycarbonyl, sec-butyl oxycarbonyl, isopentyl oxycarbonyl, 1-methylpentyl oxycarbonyl, 2-methylpentyl oxycarbonyl, 3-methylpentyl oxycarbonyl, 4-methylpentyl oxycarbonyl, 1-ethylbutyl oxycarbonyl, 2-ethylbutyl oxycarbonyl, 1-methylhexyl oxycarbonyl, 2-methylhexyl oxycarbonyl, 3-methylhexyl oxycarbonyl, 4-methylhexyl oxycarbonyl, 5-methylhexyl oxycarbonyl, 1-ethylpentyl oxycarbonyl, 2-ethylpentyl oxycarbonyl, 3-ethylpentyl oxycarbonyl, 1-propylbutyl oxycarbonyl, 1-(1-methylethyl)butyl oxycarbonyl, 1-(1-methylethyl)-2-methylpropyl oxycarbonyl, 1-methylheptyl oxycarbonyl, 2-methylheptyl oxycarbonyl, 3-methylheptyl oxycarbonyl, 4-methylheptyl oxycarbonyl, 5-methylheptyl oxycarbonyl, 6-methylheptyl oxycarbonyl, 1-ethylhexyl oxycarbonyl, 2-ethylhexyl oxycarbonyl, 3-ethylhexyl oxycarbonyl, 4-ethylhexyl oxycarbonyl, 1-n-propylpentyl oxycarbonyl, 2-propylpentyl oxycarbonyl, 1-(1-methylethyl)pentyl oxycarbonyl, 1-butylbutyl oxycarbonyl, 1-butyl-2-methylbutyl oxycarbonyl, 1-butyl-3-methylbutyl oxycarbonyl, 1-(1,1-dimethylethyl)butylbutyl oxycarbonyl, tert-butyl oxycarbonyl, 1,1-dimethylpropyl oxycarbonyl, 1,1-dimethylbutyl oxycarbonyl, 1,2-dimethylbutyl oxycarbonyl, 1,3-dimethylbutyl oxycarbonyl, 2,3-dimethylbutyl oxycarbonyl, 1-ethyl-2-methylpropyl oxycarbonyl, 1,1-dimethylpentyl oxycarbonyl, 1,2-dimethylpentyl oxycarbonyl, 1,3-dimethylpentyl oxycarbonyl, 1,4-dimethylpentyl oxycarbonyl, 2,2-dimethylpentyl oxycarbonyl, 2,3-dimethylpentyl oxycarbonyl, 2,4-dimethylpentyl oxycarbonyl, 3,3-dimethylpentyl oxycarbonyl, 3,4-dimethylpentyl oxycarbonyl, 1-ethyl-1-methylbutyl oxycarbonyl, 1-ethyl-2-methylbutyl oxycarbonyl, 1-ethyl-3-methylbutyl oxycarbonyl, 2-ethyl-1-methylbutyl oxycarbonyl, 2-ethyl-3-methylbutyl oxycarbonyl, 1,1-dimethylhexyl oxycarbonyl, 1,2-dimethylhexyl oxycarbonyl, 1,3-dimethylhexyl oxycarbonyl, 1,4-dimethylhexyl oxycarbonyl, 1,5-dimethylhexyl oxycarbonyl, 2,2-dimethylhexyl oxycarbonyl, 2,3-dimethylhexyl oxycarbonyl, 2,4-dimethylhexyl oxycarbonyl, 2,5-dimethylhexyl oxycarbonyl, 3,3-dimethylhexyl oxycarbonyl, 3,4-dimethylhexyl oxycarbonyl, 3,5-dimethylhexyl oxycarbonyl, 4,4-dimethylhexyl oxycarbonyl, 4,5-dimethylhexyl oxycarbonyl, 1-ethyl-2-methylpentyl oxycarbonyl, 1-ethyl-3-methylpentyl oxycarbonyl, 1-ethyl-4-methylpentyl oxycarbonyl, 2-ethyl-1-methylpentyl oxycarbonyl, 2-ethyl-2-methylpentyl oxycarbonyl, 2-ethyl-3-methylpentyl oxycarbonyl, 2-ethyl-4-methylpentyl oxycarbonyl, 3-ethyl-1-methylpentyl oxycarbonyl, 3-ethyl-2-methylpentyl oxycarbonyl, 3-ethyl-3-methylpentyl oxycarbonyl, 3-ethyl-4-methylpentyl oxycarbonyl, 1-propyl-1-methylbutyl oxycarbonyl, 1-propyl-2-methylbutyl oxycarbonyl, 1-propyl-3-methylbutyl oxycarbonyl, 1-(1-methylethyl)-1-methylbutyl oxycarbonyl, 1-(1-methylethyl)-2-methylbutyl oxycarbonyl, 1-(1-methylethyl)-3-methylbutyl oxycarbonyl, 1,1-diethylbutyl oxycarbonyl, and 1,2-diethylbutyl oxycarbonyl)); or

[5] a $C_{1-8}$ ether group
(examples include (1) a group formed by introducing at least one (e.g., 1, 2, 3, or 4) ether oxygen into alkyl listed in [1] above and (2) a $C_{1-8}$ ether group represented by each of the following formulas: $H-C_pH_{2p}-O-C_qH_{2q}-$ wherein p is 1 to 7, q is 1 to 7, and p+q is 2 to 8; $H-C_pH_{2p}-O-C_qH_{2q}-O-C_rH_{2r}-$ wherein p is 1 to 6, q is 1 to 6, r is 1 to 6, and p+q+r is 3 to 8; and $H-C_pH_{2p}-O-C_qH_{2q}-O-C_rH_{2r}-O-C_sH_{2s}-$ wherein p is 1 to 6, q is 1 to 6, r is 1 to 6, and p+q+r+s is 4 to 8 (in these formulas, the alkylene chains represented by $C_pH_{2p}$, $C_qH_{2q}$, $C_rH_{2r}$, or $C_sH_{2s}$ may be independently a linear or branched chain)).

$R^3$ is still more preferably methyl, hexyl, 2-ethylhexyl, $CH_3-(CH_2)_2-O-CH_2-$, or $CH_3-O-(CH_2)_2-O-(CH_2)^2-O-CH_2-$.

In particular, when $R^3$ is alkyl or alkyl ether, the fullerene derivative of the present invention can further exhibit high solubility in an organic solvent. Examples of the organic solvent include carbon disulfide, chloroform, dichloroethane, toluene, xylene, chlorobenzene, and dichlorobenzene. Thus, when the fullerene derivative of the present invention is used in, for example, an n-type semiconductor for photoelectric conversion elements, such as organic thin-film solar cells, the fullerene derivative suitably dissolves in an organic solvent in the production of such a semiconductor; as a result, operability in preparing a device through a coating process is improved, and the n-type semiconductor as a material can suitably be arranged in the obtained device, making it possible to produce an organic thin-film solar cell that exhibits excellent performance.

$R^4$ is preferably a hydrogen atom, alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

Examples of the substituent and the number of substituents in "alkyl optionally substituted with at least one substituent," "alkenyl optionally substituted with at least one substituent," "alkynyl optionally substituted with at least one substituent," "aryl optionally substituted with at least one substituent," "ether optionally substituted with at least one substituent," and "ester optionally substituted with at least one substituent" all represented by $R^4$ are those described the examples of substituents and the number of substituents for "aryl optionally substituted with at least one substituent" represented by $R^1$.

In a preferable embodiment of the present invention, $R^4$ is

[1] a $C_{1-8}$ alkyl group
(examples include (a) linear $C_{1-8}$ alkyl (e.g., methyl, ethyl, n-propyl, n-butyl, n-pentyl, n-hexyl, n-heptyl, and n-octyl); and
(b) branched alkyl (e.g., isopropyl, isobutyl, sec-butyl, isopentyl, 1-methylpentyl, 2-methylpentyl, 3-methylpentyl, 4-methylpentyl, 1-ethylbutyl, 2-ethylbutyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1-(1-methylethyl)butyl, 1-(1-methylethyl)-2-methylpropyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-n-propylpentyl, 2-propylpentyl, 1-(1-methylethyl) pentyl, 1-butylbutyl, 1-butyl-2-methylbutyl, 1-butyl-3-methylbutyl, 1-(1,1-dimethylethyl)butylbutyl, tert-butyl, 1,1-dimethylpropyl, 1,1-dimethylbutyl, 1,2-dimethylbutyl, 1,3-dimethylbutyl, 2,3-dimethylbutyl, 1-ethyl-2-methylpropyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethyl-1-methylbutyl, 1-ethyl-2-methylbutyl, 1-ethyl-3-methylbutyl, 2-ethyl-1-methylbutyl, 2-ethyl-3-methylbutyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 1-ethyl-2-methylpentyl, 1-ethyl-3-methylpentyl, 1-ethyl-4-methylpentyl, 2-ethyl-1-methylpentyl, 2-ethyl-2-methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1-propyl-1-methylbutyl, 1-propyl-2-methylbutyl, 1-propyl-3-methylbutyl, 1-(1-methylethyl)-

1-methylbutyl, 1-(1-methylethyl)-2-methylbutyl, 1-(1-methylethyl)-3-methylbutyl, 1,1-diethylbutyl, and 1,2-diethylbutyl));

[2] a $C_{1-8}$ alkyloxy group
(examples include (a) linear $C_{1-8}$ alkyloxy (e.g., methyloxy, ethyloxy, n-propyloxy, n-butyloxy, n-pentyloxy, n-hexyloxy, n-heptyloxy, and n-octyloxy); and (b) branched $C_{3-8}$ alkyloxy (e.g., isopropyloxy, isobutyloxy, sec-butyloxy, isopentyloxy, 1-methylpentyloxy, 2-methylpentyloxy, 3-methylpentyloxy, 4-methylpentyloxy, 1-ethylbutyloxy, 2-ethylbutyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylbutyloxy, 1-(1-methylethyl)butyloxy, 1-(1-methylethyl)-2-methylpropyloxy, 1-methylheptyloxy, 2-methylheptyloxy, 3-methylheptyloxy, 4-methylheptyloxy, 5-methylheptyloxy, 6-methylheptyloxy, 1-ethylhexyloxy, 2-ethylhexyloxy, 3-ethylhexyloxy, 4-ethylhexyloxy, 1-n-propylpentyloxy, 2-propylpentyloxy, 1-(1-methylethyl)pentyloxy, 1-butylbutyloxy, 1-butyl-2-methylbutyloxy, 1-butyl-3-methylbutyloxy, 1-(1,1-dimethylethyl)butylbutyloxy, tert-butyloxy, 1,1-dimethylpropyloxy, 1,1-dimethylbutyloxy, 1,2-dimethylbutyloxy, 1,3-dimethylbutyloxy, 2,3-dimethylbutyloxy, 1-ethyl-2-methylpropyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 1-ethyl-1-methylbutyloxy, 1-ethyl-2-methylbutyloxy, 1-ethyl-3-methylbutyloxy, 2-ethyl-1-methylbutyloxy, 2-ethyl-3-methylbutyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-dimethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 1-ethyl-2-methylpentyloxy, 1-ethyl-3-methylpentyloxy, 1-ethyl-4-methylpentyloxy, 2-ethyl-1-methylpentyloxy, 2-ethyl-2-methylpentyloxy, 2-ethyl-3-methylpentyloxy, 2-ethyl-4-methylpentyloxy, 3-ethyl-1-methylpentyloxy, 3-ethyl-2-methylpentyloxy, 3-ethyl-3-methylpentyloxy, 3-ethyl-4-methylpentyloxy, 1-propyl-1-methylbutyloxy, 1-propyl-2-methylbutyloxy, 1-propyl-3-methylbutyloxy, 1-(1-methylethyl)-1-methylbutyloxy, 1-(1-methylethyl)-2-methylbutyloxy, 1-(1-methylethyl)-3-methylbutyloxy, 1,1-diethylbutyloxy, and 1,2-diethylbutyloxy))

[3] a $C_{1-8}$ alkyl-carbonyloxy group;
(examples include (a) linear $C_{1-8}$ alkyl-carbonyloxy (e.g., methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, and n-octylcarbonyloxy); and (b) branched $C_{3-8}$ alkyl-carbonyloxy (e.g., isopropyl carbonyloxy, isobutyl carbonyloxy, sec-butyl carbonyloxy, isopentyl carbonyloxy, 1-methylpentyl carbonyloxy, 2-methylpentyl carbonyloxy, 3-methylpentyl carbonyloxy, 4-methylpentyl carbonyloxy, 1-ethylbutyl carbonyloxy, 2-ethylbutyl carbonyloxy, 1-methylhexyl carbonyloxy, 2-methylhexyl carbonyloxy, 3-methylhexyl carbonyloxy, 4-methylhexyl carbonyloxy, 5-methylhexyl carbonyloxy, 1-ethylpentyl carbonyloxy, 2-ethylpentyl carbonyloxy, 3-ethylpentyl carbonyloxy, 1-propylbutyl carbonyloxy, 1-(1-methylethyl)butyl carbonyloxy, 1-(1-methylethyl)-2-methylpropyl carbonyloxy, 1-methylheptyl carbonyloxy, 2-methylheptyl carbonyloxy, 3-methylheptyl carbonyloxy, 4-methylheptyl carbonyloxy, 5-methylheptyl carbonyloxy, 6-methylheptyl carbonyloxy, 1-ethylhexyl carbonyloxy, 2-ethylhexyl carbonyloxy, 3-ethylhexyl carbonyloxy, 4-ethylhexyl carbonyloxy, 1-n-propylpentyl carbonyloxy, 2-propylpentyl carbonyloxy, 1-(1-methylethyl)pentyl carbonyloxy, 1-butylbutyl carbonyloxy, 1-butyl-2-methylbutyl carbonyloxy, 1-butyl-3-methylbutyl carbonyloxy, 1-(1,1-dimethylethyl)butylbutyl carbonyloxy, tert-butyl carbonyloxy, 1,1-dimethylpropyl carbonyloxy, 1,1-dimethylbutyl carbonyloxy, 1,2-dimethylbutyl carbonyloxy, 1,3-dimethylbutyl carbonyloxy, 2,3-dimethylbutyl carbonyloxy, 1-ethyl-2-methylpropyl carbonyloxy, 1,1-dimethylpentyl carbonyloxy, 1,2-dimethylpentyl carbonyloxy, 1,3-dimethylpentyl carbonyloxy, 1,4-dimethylpentyl carbonyloxy, 2,2-dimethylpentyl carbonyloxy, 2,3-dimethylpentyl carbonyloxy, 2,4-dimethylpentyl carbonyloxy, 3,3-dimethylpentyl carbonyloxy, 3,4-dimethylpentyl carbonyloxy, 1-ethyl-1-methylbutyl carbonyloxy, 1-ethyl-2-methylbutyl carbonyloxy, 1-ethyl-3-methylbutyl carbonyloxy, 2-ethyl-1-methylbutyl carbonyloxy, 2-ethyl-3-methylbutyl carbonyloxy, 1,1-dimethylhexyl carbonyloxy, 1,2-dimethylhexyl carbonyloxy, 1,3-dimethylhexyl carbonyloxy, 1,4-dimethylhexyl carbonyloxy, 1,5-dimethylhexyl carbonyloxy, 2,2-dimethylhexyl carbonyloxy, 2,3-dimethylhexyl carbonyloxy, 2,4-dimethylhexyl carbonyloxy, 2,5-dimethylhexyl carbonyloxy, 3,3-dimethylhexyl carbonyloxy, 3,4-dimethylhexyl carbonyloxy, 3,5-dimethylhexyl carbonyloxy, 4,4-dimethylhexyl carbonyloxy, 4,5-dimethylhexyl carbonyloxy, 1-ethyl-2-methylpentyl carbonyloxy, 1-ethyl-3-methylpentyl carbonyloxy, 1-ethyl-4-methylpentyl carbonyloxy, 2-ethyl-1-methylpentyl carbonyloxy, 2-ethyl-2-methylpentyl carbonyloxy, 2-ethyl-3-methylpentyl carbonyloxy, 2-ethyl-4-methylpentyl carbonyloxy, 3-ethyl-1-methylpentyl carbonyloxy, 3-ethyl-2-methylpentyl carbonyloxy, 3-ethyl-3-methylpentyl carbonyloxy, 3-ethyl-4-methylpentyl carbonyloxy, 1-propyl-1-methylbutyl carbonyloxy, 1-propyl-2-methylbutyl carbonyloxy, 1-propyl-3-methylbutyl carbonyloxy, 1-(1-methylethyl)-1-methylbutyl carbonyloxy, 1-(1-methylethyl)-2-methylbutyl carbonyloxy, 1-(1-methylethyl)-3-methylbutyl carbonyloxy, 1,1-diethylbutyl carbonyloxy, and 1,2-diethylbutyl carbonyloxy))

[4] a $C_{1-8}$ alkyl-oxycarbonyl group
(examples include (a) linear $C_{1-8}$ alkyl-oxycarbonyl (e.g., methyloxycarbonyl, ethyloxycarbonyl, n-propyloxycarbonyl, n-butyloxycarbonyl, n-pentyloxycarbonyl, n-hexyloxycarbonyl, n-heptyloxycarbonyl, and n-octyloxycarbonyl); and (b) branched $C_{3-8}$ alkyl-oxycarbonyl (e.g., isopropyl oxycarbonyl, isobutyl oxycarbonyl, sec-butyl oxycarbonyl, isopentyl oxycarbonyl, 1-methylpentyl oxycarbonyl, 2-methylpentyl oxycarbonyl, 3-methylpentyl oxycarbonyl, 4-methylpentyl oxycarbonyl, 1-ethylbutyl oxycarbonyl, 2-ethylbutyl oxycarbonyl, 1-methylhexyl oxycarbonyl, 2-methylhexyl oxycarbonyl, 3-methylhexyl oxycarbonyl, 4-methylhexyl oxycarbonyl, 5-methylhexyl oxycarbonyl, 1-ethylpentyl oxycarbonyl, 2-ethylpentyl oxycarbonyl, 3-ethylpentyl oxycarbonyl, 1-propylbutyl oxycarbonyl, 1-(1-methylethyl)butyl oxycarbonyl, 1-(1-methylethyl)-2-methylpropyl oxycarbonyl, 1-methylheptyl oxycarbonyl, 2-methylheptyl oxycarbonyl, 3-methylheptyl oxycarbonyl, 4-methylheptyl oxycarbonyl, 5-methylheptyl oxycarbonyl, 6-methylheptyl oxycarbonyl, 1-ethylhexyl oxycarbonyl, 2-ethylhexyl oxycarbonyl, 3-ethylhexyl oxycarbonyl, 4-ethylhexyl oxycarbonyl, 1-n-propylpentyl oxycarbonyl, 2-propylpentyl oxycarbonyl, 1-(1-methylethyl)pentyl oxycarbonyl, 1-butylbutyl oxycarbonyl, 1-butyl-2-methylbutyl oxycarbonyl, 1-butyl-3-methylbutyl oxycarbonyl, 1-(1,1-dimethylethyl)butylbutyl oxycarbonyl, tert-butyl oxycarbonyl, 1,1-dimethylpropyl oxycarbonyl, 1,1-dimethylbutyl oxycarbonyl, 1,2-dimethylbutyl oxycarbonyl, 1,3-dimethylbutyl oxycarbonyl, 2,3-dimethylbutyl oxycarbonyl, 1-ethyl-2-methylpropyl oxycarbonyl, 1,1-dimethylpentyl oxycarbonyl, 1,2-dimethylpentyl oxycarbonyl, 1,3-dimethylpentyl oxycarbonyl, 1,4-dimethylpentyl oxycarbonyl, 2,2-dimethylpentyl oxycarbonyl, 2,3-dimethylpentyl oxycarbonyl, 2,4-dimethylpentyl oxycarbonyl, 3,3-dimethylpentyl oxycarbonyl, 3,4-dimethylpentyl oxycarbonyl, 1-ethyl-1-methylbutyl oxycarbonyl, 1-ethyl-2-methylbutyl oxycarbonyl, 1-ethyl-3-methylbutyl oxycarbonyl, 2-ethyl-1-methylbutyl oxycarbonyl, 2-ethyl-3-methylbutyl oxycarbonyl, 1,1-dimethylhexyl oxycarbonyl, 1,2-dimethylhexyl oxycarbonyl, 1,3-dimethylhexyl oxycarbonyl, 1,4-dimethylhexyl oxycarbonyl, 1,5-dimethylhexyl oxycarbonyl, 2,2-dimethylhexyl oxycarbonyl, 2,3-dimethylhexyl oxycarbonyl, 2,4-dimethylhexyl oxycarbonyl, 2,5-dimethylhexyl oxycarbonyl, 3,3-dimethylhexyl oxycarbonyl, 3,4-dimethylhexyl oxycarbonyl, 3,5-dimethylhexyl oxycarbonyl, 4,4-dimethylhexyl oxycarbonyl, 4,5-dimethylhexyl oxycarbonyl, 1-ethyl-2-methylpentyl oxycarbonyl, 1-ethyl-3-methylpentyl oxycarbonyl, 1-ethyl-4-methylpentyl oxycarbonyl, 2-ethyl-1-methylpentyl oxycarbonyl, 2-ethyl-2-methylpentyl oxycarbonyl, 2-ethyl-3-methylpentyl oxycarbonyl, 2-ethyl-4-methylpentyl oxycarbonyl, 3-ethyl-1-methylpentyl oxycarbonyl, 3-ethyl-2-methylpentyl oxycarbonyl, 3-ethyl-3-methylpentyl oxycarbonyl, 3-ethyl-4-methylpentyl oxycarbonyl, 1-propyl-1-methylbutyl oxycarbonyl, 1-propyl-2-methylbutyl oxycarbonyl, 1-propyl-3-methylbutyl oxycarbonyl, 1-(1-methylethyl)-1-methylbutyl oxycarbonyl, 1-(1-methylethyl)-2-methylbutyl oxycarbonyl, 1-(1-methylethyl)-3-methylbutyl oxycarbonyl, 1,1-diethylbutyl oxycarbonyl, and 1,2-diethylbutyl oxycarbonyl));

[5] a $C_{1-8}$ ether group
(examples include (1) a group formed by introducing at least one (e.g., 1, 2, 3, or 4) ether oxygen into alkyl listed in [1] above and (2) a $C_{1-8}$ ether group represented by each of the following formulas:
H—$C_pH_{2p}$—O—$C_qH_{2q}$— wherein p is 1 to 7, q is 1 to 7, and p+q is 2 to 8; H—$C_pH_{2p}$—O—$C_qH_{2q}$—O—$C_rH_{2r}$— wherein p is 1 to 6, q is 1 to 6, r is 1 to 6, and p+q+r is 3 to 8; and H—$C_pH_{2p}$—O—$C_qH_{2q}$—O—$C_rH_{2r}$—O—$C_sH_{2s}$— wherein p is 1 to 6, q is 1 to 6, r is 1 to 6, and p+q+r+s is 4 to 8 (in these formulas, the alkylene chains represented by $C_pH_{2p}$, $C_qH_{2q}$, $C_rH_{2r}$, or $C_sH_{2s}$ may be independently a linear or branched chain)); or

[6] phenyl, naphthyl, or pyrenyl each optionally substituted with at least one substituent selected from the group consisting of fluorine, methyl, groups listed in [1] to [5], and cyano; or

[7] a hydrogen atom.

$R^4$ is more preferably a hydrogen atom or alkyl having 1 to 8 carbon atoms.

$R^4$ is still more preferably a hydrogen atom or methyl.

In a preferable embodiment of the present invention, $R^3$ is methyl, hexyl, 2-ethylhexyl, $CH_3$—$(CH_2)_2$—O—$CH_2$—, or $CH_3$—O—$(CH_2)_2$—O—$(CH_2)_2$—O—$CH_2$—, and $R^4$ is a hydrogen atom or methyl.

In a preferable embodiment of the present invention, $R^2$ and $R^3$ are alkyl.

In a preferable embodiment of the present invention, $R^3$ and $R^4$ are both alkyl (preferably methyl).

In a preferable embodiment of the present invention, $R^1$ is phenyl optionally substituted with at least one fluorine atom; $R^2$ is alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent; and $R^3$ and $R^4$ are identical or different and are a hydrogen atom, alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

As described above, at least one of $R^2$ and $R^3$ is alkyl optionally substituted with at least one substituent or alkyl ether optionally substituted with at least one substituent.

In a preferable embodiment of the present invention, $R^1$ is phenyl, $R^2$ is hexyl or phenyl, $R^3$ is methyl, hexyl, 2-ethylhexyl, $CH_3$—$(CH_2)_2$—O—$CH_2$—, or $CH_3$—O—$(CH_2)_2$—O—$(CH_2)_2$—O—$CH_2$—, and $R^4$ is hydrogen or methyl.

In a preferable embodiment of the present invention, $R^1$ is phenyl, $R^2$ is aryl, $R^3$ is alkyl, and $R^4$ is hydrogen.

Although this would be easily understood by a person skilled in the art and is described simply for confirmation, the compound in this embodiment has the same structure as that of a compound wherein $R^1$ is phenyl, $R^2$ is alkyl, $R^3$ is aryl, and $R^4$ is hydrogen.

Because of $R^1$, $R^2$, $R^3$, and $R^4$ forming such a chemical structure, when the fullerene derivative of the present invention is used in, for example, an n-type semiconductor for photoelectric conversion elements, such as organic thin-film solar cells, the fullerene derivative can provide a high voltage. Additionally, when $R^3$ or $R^4$, or both are alkyl as described above, the fullerene derivative exhibits high solubility in a solvent, and this makes it possible to produce organic thin-film solar cells that exhibit excellent performance.

Ring A is preferably a $C_{60}$ fullerene or a $C_{70}$ fullerene, and more preferably a $C_{60}$ fullerene.

The fullerene derivative represented by formula (1) may be a mixture of a fullerene derivative wherein ring A is a $C_{60}$ fullerene (which hereinafter may be referred to as a "$C_{60}$ fullerene derivative"), and a fullerene derivative wherein ring A is a $C_{70}$ fullerene (which hereinafter may be referred to as a "$C_{70}$ fullerene derivative").

The content ratio of the $C_{60}$ fullerene derivative to the $C_{70}$ fullerene derivative in the mixture may be, for example, 99.999:0.001 to 0.001:99.999, 99.99:0.01 to 0.01:99.99, 99.9:0.1 to 0.1:99.9, 99:1 to 1:99, 95:5 to 5:95, 90:10 to 10:90, or 80:20 to 20:80 on a molar ratio basis.

The content ratio of the $C_{60}$ fullerene derivative to the $C_{70}$ fullerene derivative is preferably 80:20 to 50:50, and more preferably 80:20 to 60:40.

The content of the $C_{60}$ fullerene derivative in the mixture may be, for example, 0.001 to 99.999 mass %, 0.01 to 99.99 mass %, 0.1 to 99.9 mass %, 1 to 99 mass %, 5 to 95 mass %, 10 to 90 mass %, or 20 to 80 mass %.

The content of the $C_a$ fullerene derivative is preferably 50 to 80 mass %, and more preferably 60 to 80 mass %.

The content of the $C_{70}$ fullerene derivative in the mixture may be, for example, 0.001 to 99.999 mass %, 0.01 to 99.99 mass %, 0.1 to 99.9 mass %, 1 to 99 mass %, 5 to 95 mass %, 10 to 90 mass %, or 20 to 80 mass %.

The content of the $C_{70}$ fullerene derivative is preferably 20 to 50 mass %, and more preferably 20 to 40 mass %.

The mixture may essentially consist of the $C_{60}$ fullerene derivative and the $C_{70}$ fullerene derivative.

The mixture may consist of the $C_{60}$ fullerene derivative and the $C_{70}$ fullerene derivative.

The mixture may be a mixture of the $C_{60}$ fullerene derivative and the $C_{70}$ fullerene derivative.

In this specification, the $C_{60}$ fullerene may be represented by the following structural formula, as is common in this technical field.

Thus, when ring A is a $C_{60}$ fullerene, the fullerene derivative represented by formula (1) can be represented by the following formula.

Because the fullerene derivative of the present invention exhibits excellent solubility in various organic solvents, the fullerene derivative makes it easy to form a thin film by a coating technique.

Additionally, the fullerene derivative of the present invention makes it easy to form a bulk heterojunction structure when used as an n-type semiconductor material together with an organic p-type semiconductor material in the production of an organic power-generating layer.

The fullerene derivative of the present invention exhibits high conversion efficiency and enables high voltage output.

The present invention also provides a fullerene derivative that has an LUMO level of −3.65 eV or more (1) and that has a solubility in toluene at room temperature of 0.5% or more (2).

The LUMO level can be measured by a method according to Karakawa et al., Journal of Materials Chemistry A, 2014, vol. 2, p. 20889.

The solubility in toluene at room temperature can be determined from the absorbance in accordance with the Beer-Lambert law. First, a molar extinction coefficient is determined using a fullerene derivative toluene solution of a known concentration. A predetermined amount of the supernatant of a supersaturated fullerene derivative toluene solution is weighed, and the absorbance of this solution is measured. The concentration is calculated from the following equation.

$$C = A/\varepsilon d$$

wherein C is a concentration; A is an absorbance; $\varepsilon$ is a molar extinction coefficient; and d is a cell length for absorbance measurement (1 cm)

Preferable examples of such a fullerene derivative include the fullerene derivatives described above.

A preferable embodiment of the present invention can be the fullerene derivative according to any one of Items 1 to 5 that has an LUMO level of −3.65 eV or more (1), and that has a solubility in toluene at room temperature of 0.5% or more (2).

Method for Producing a Fullerene Derivative

The fullerene derivative of the present invention can be produced by a known method for producing a fullerene derivative, or by a method complying with the method.

Specifically, the fullerene derivative of the present invention can be synthesized, for example, in accordance with the following scheme. The symbols in the scheme are as defined above, and the symbols in formulas (a) and (b) correspond to those in formula (1) for easy understanding for a person skilled in the art.

Step A

In step A, a glycine derivative (compound (b)) is reacted with an aldehyde compound (compound (a)) and a fullerene (compound (c)) to thereby obtain a fullerene derivative (compound (1)) represented by formula (1).

Although the amount ratio of the aldehyde compound (compound (a)), the glycine derivative (compound (b)), and the fullerene (compound (c)) is arbitrarily determined, the aldehyde compound (compound (a)) and the glycine derivative (compound (b)) are each typically added in an amount of 0.1 to 10 moles, and preferably 0.5 to 2 moles, per mole of the fullerene (compound (c)), from the standpoint of achieving high yield.

The reaction is performed without a solvent or in a solvent. Examples of solvents include carbon disulfide, chloroform, dichloroethane, toluene, xylene, chlorobenzene, and dichlorobenzene. Of these, chloroform, toluene, xylene, and chlorobenzene are preferable. These solvents may also be mixed in suitable proportions.

The reaction temperature is typically within the range of room temperature to about 150° C., and preferably within the range of about 80 to about 120° C. In this specification, the room temperature is within the range of 15 to 30° C.

The reaction time is typically within the range of about 1 hour to about 4 days, and preferably within the range of about 10 to about 24 hours.

The obtained compound (1) can optionally be purified by a conventional purification method. For example, the obtained compound (1) can be purified by silica gel column chromatography (as a developing solvent, for example, hexane-chloroform, hexane-toluene, or hexane-carbon disulfide is preferably used), and further purified by HPLC (preparative GPC) (as a developing solvent, for example, chloroform or toluene is preferably used).

The aldehyde compound (compound (a)), the glycine derivative (compound (b)), and the fullerene (compound (c)) used in step A are all known compounds; these compounds can be synthesized by a known method or a method complying with a known method, and are also commercially available.

Specifically, the aldehyde compound (compound (a)) can be synthesized, for example, by method (a1), (a2), or (a3) described below.

In the reaction formulas describing these methods, $R^2$ is as defined in formula (1), and corresponds to $R^2$ of the target fullerene derivative.

Method (a1): Oxidation of Alcohol Represented by $R^2$—$CH_2OH$

For oxidation in this method, for example, the following known methods can be used: (i) a method using chromic acid, manganese oxide, or the like as an oxidant, (ii) Swern oxidation using dimethyl sulfoxide as an oxidant, or (iii) an oxidation method using hydrogen peroxide, oxygen, air, or the like in the presence of a catalyst.

Method (a2): Reduction of Carboxylic Acid Represented by $R^2$—COOH, Acid Halide Thereof, Ester Thereof, or Acid Amide Thereof For reduction in this method, for example, the following known methods can be used: (i) a method using metal hydride as a reducing agent, (ii) a method for hydrogen reduction in the presence of a catalyst, or (iii) a method using hydrazine as a reducing agent.

Method (a3): Carbonylation of Halide Represented by $R^2$—X (X Represents a Halogen)

For carbonylation in this method, for example, a method including forming an anion from the halide described above using n-BuLi and introducing a carbonyl group thereinto can be used. As a carbonyl group-introducing reagent, amide compounds, such as N,N-dimethylformamide (DMF) or N-formyl derivatives of piperidine, morpholine, piperazine, or pyrrolidine can be used.

Specifically, the glycine derivative (compound (b)) can be synthesized, for example, by method (b1), (b2), or (b3) described below.

Method (b1): Reaction between Aniline Derivative and Halogenated Acetic Acid

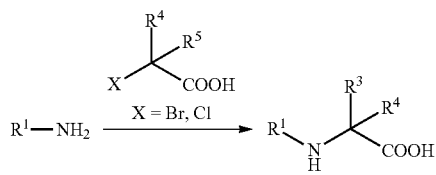

This reaction can use water, methanol, ethanol, or a mixture thereof as a solvent, and can be carried out optionally in the presence of a base.

Method (b2): Reaction between Aniline Derivative and Halogenated Acetic Acid Ester, and Hydrolysis of Glycine Derivative Ester Obtained by Reaction

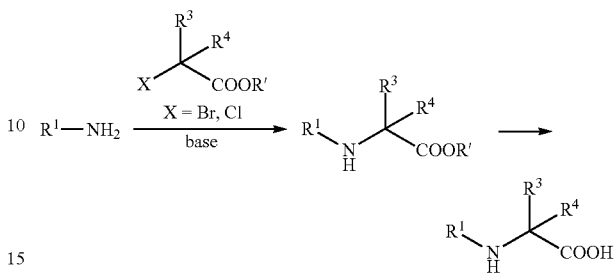

In this method, the reaction between an aniline derivative and a halogenated acetic acid ester can use, for example, methanol or ethanol as a solvent, and can be carried out in the presence of a base such as acetate, carbonate, phosphate, and tertiary amine. The hydrolysis of a glycine derivative ester can typically be carried out in the presence of a water-soluble alkali at room temperature.

Method (b3): Reaction between Aromatic Halide and Glycine

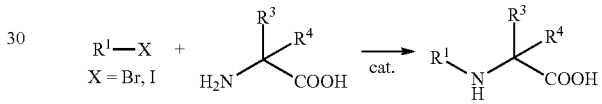

The reaction uses, for example, monovalent copper as a catalyst, and can be carried out in the presence of a bulky amine, an amino acid, an amino alcohol, or the like. Preferable reaction solvents for use include water, methanol, ethanol, and a mixture thereof. The reaction temperature is from room temperature to about 100° C.

As described above, the fullerene derivative of the present invention can be synthesized by a simple method using a glycine derivative and an aldehyde derivative as starting materials; thus, the fullerene derivative can be produced at low cost.

Use of Fullerene Derivative

The fullerene derivative of the present invention can be suitably used as an n-type semiconductor material, in particular as an n-type semiconductor material for photoelectric conversion elements such as organic thin-film solar cells.

When used as an n-type semiconductor material, the fullerene derivative of the present invention is typically used in combination with an organic p-type semiconductor material (organic p-type semiconductor compound).

Examples of organic p-type semiconductor materials include poly-3-hexylthiophene (P3HT), poly-p-phenylenevinylene, poly-alkoxy-p-phenylenevinylene, poly-9,9-dialkylfluorene, and poly-p-phenylenevinylene.

Because of the many approaches to use these materials in solar cells in the past and their ready availability, these materials can easily provide devices that exhibit stable performance.

To achieve higher conversion efficiency, donor-acceptor π-conjugated polymers capable of absorbing long-wavelength light because of their narrowed bandgap (low bandgap) are effective.

These donor-acceptor π-conjugated polymers comprise donor units and acceptor units, which are alternately positioned.

Examples of usable donor units include benzodithiophene, dithienosilole, and N-alkyl carbazole, and examples of usable acceptor units include benzothiadiazole, thienothiophene, and thiophene pyrrole dione.

Specific examples include high-molecular compounds obtained by combining these units, such as poly(thieno[3,4-b]thiophene-co-benzo[1,2-b:4,5-b']thiophene) (PTBx series), and poly(dithieno[1,2-b:4,5-b'][3,2-b:2',3'-d]silole-alt-(2,1,3-benzothiadiazole).

Of these, the following are preferable:
(1) poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7, the structural formula is shown below);
(2) poly[(4,8-di(2-ethylhexyloxy)benzo[1,2-b:4,5-b']dithiophene)-2,6-diyl-alt-((5-octylthieno[3,4-c]pyrrol-4,6-dione)-1,3-diyl) (PBDTTPD, the structural formula is shown below);
(3) poly[(4,4'-bis(2-ethylhexyl)dithieno[3,2-b:2',3'-d]silole)-2,6-diyl-alt-(2,1,3-benzothiadiazole)-4,7-diyl] (PSBTBT, the structural formula is shown below);
(4) poly[N-9''-heptadecanyl-2,7-carbazole-alt-5,5-(4',7'-di-2-thienyl-2',1',3'-benzothiadiazole)](PCDTBT, the structural formula is shown below); and
(5) poly[1-(6-{4,8-bis[(2-ethylhexyl)oxy]-6-methylbenzo[1,2-b:4,5-b']dithiophene-2-yl}{3-fluoro-4-methylthieno[3,4-b]thiophene-2-yl}-1-octanone) (PBDTTT-CF, the structural formula is shown below).

Of these, more preferable are PTB-based compounds containing, as an acceptor unit, thieno[3,4-b]thiophene having a fluorine atom at position 3, and particularly preferable examples include PBDTTT-CF and PTB7.

PBDTTPD

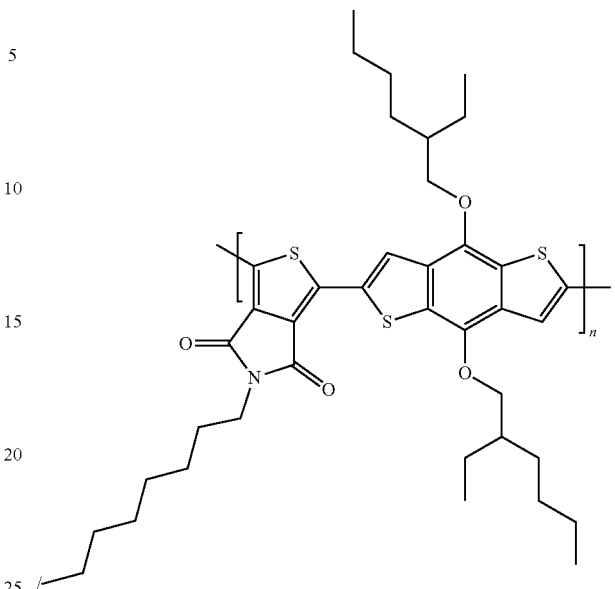

wherein n represents the number of repeating units.

PTB7

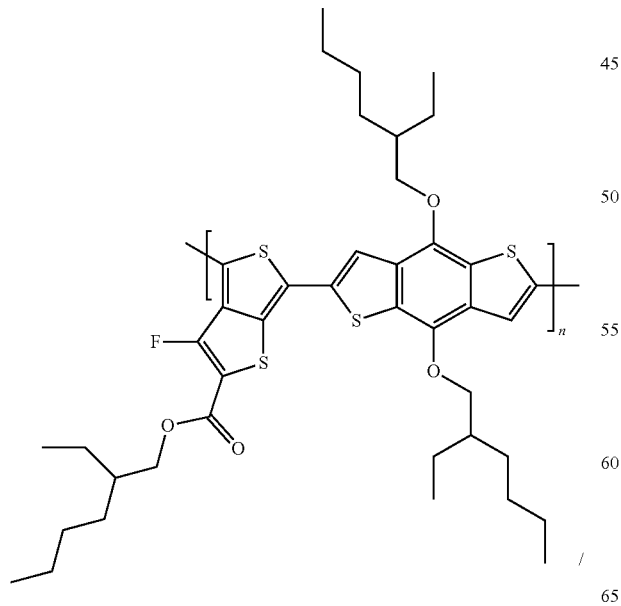

wherein n represents the number of repeating units.

PSBTBT

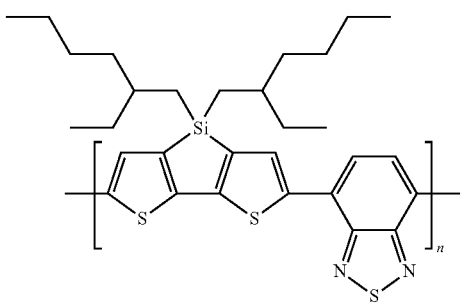

wherein n represents the number of repeating units.

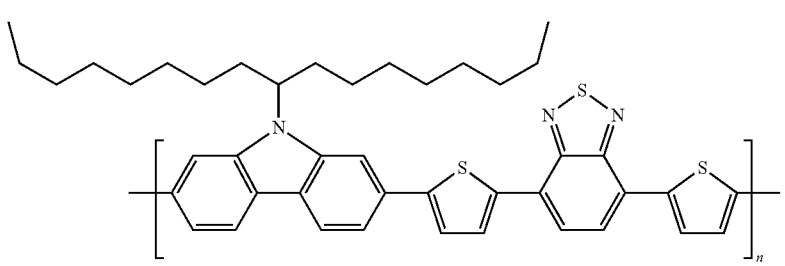

PCDTBT wherein n represents the number of repeating units.

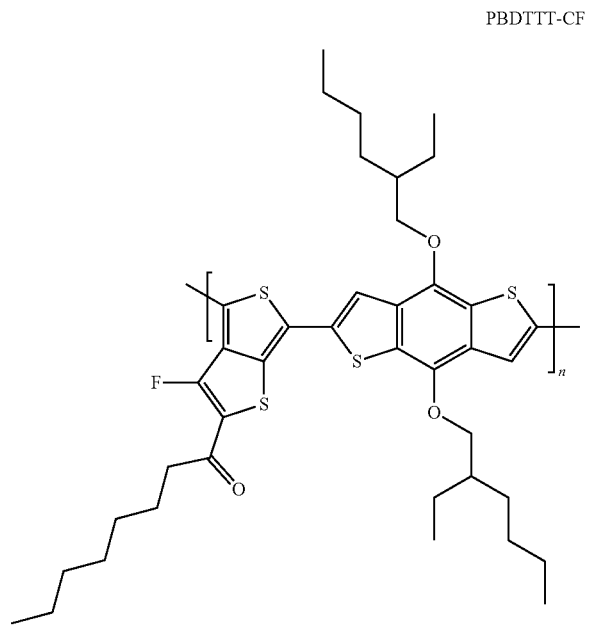

PBDTTT-CF wherein n represents the number of repeating units.

An organic power-generating layer prepared using the fullerene derivative of the present invention as an n-type semiconductor material in combination with an organic p-type semiconductor material can achieve high conversion efficiency.

Because of its excellent solubility in various organic solvents, the fullerene derivative of the present invention, when used as an n-type semiconductor material, enables the preparation of an organic power-generating layer by a coating technique, and also simplifies the preparation of an organic power-generating layer having a large area.

The fullerene derivative of the present invention is a compound having excellent compatibility with organic p-type semiconductor materials and suitable self-aggregating properties. Thus, it is easy to form an organic power-generating layer having a bulk junction structure using the fullerene derivative as an n-type semiconductor material (organic n-type semiconductor material). The use of this organic power-generating layer enables the production of an organic thin-film solar cell or photosensor that exhibits high conversion efficiency.

Accordingly, the use of the fullerene derivative of the present invention as an n-type semiconductor material enables the production of an organic thin-film solar cell exhibiting excellent performance at low cost.

An alternative application of the organic power-generating layer comprising (or consisting of) the n-type semiconductor material of the present invention is the use of the layer in an image sensor for digital cameras. While digital cameras are required to have advanced functions (higher definition), existing image sensors composed of a silicon semiconductor suffer from decreased sensitivity. To address this situation, an image sensor composed of an organic material with high photosensitivity is expected to achieve higher sensitivity and higher definition. Materials for forming the light-receiving part of such a sensor need to absorb light highly sensitively and generate an electrical signal from that light highly efficiently. To meet this demand, an organic power-generating layer comprising (or consisting of) the n-type semiconductor material of the present invention can provide a high functionality as a material for the image sensor light-receiving part described above, because of its ability to efficiently convert visible light into electrical energy.

n-Type Semiconductor Material

The n-type semiconductor material of the present invention consists of the fullerene derivative of the present invention.

Organic Power-Generating Layer

The organic power-generating layer of the present invention comprises the fullerene derivative of the present invention as an n-type semiconductor material (n-type semiconductor compound).

The organic power-generating layer of the present invention can be a light conversion layer (photoelectric conversion layer).

The organic power-generating layer of the present invention typically comprises the organic p-type semiconductor material mentioned above (organic p-type semiconductor compound) in combination with the fullerene derivative of the present invention, i.e., the n-type semiconductor material of the present invention.

The organic power-generating layer of the present invention typically consists of the n-type semiconductor material of the present invention and the organic p-type semiconductor material.

The organic power-generating layer of the present invention preferably has a bulk heterojunction structure formed by the n-type semiconductor material of the present invention and the organic p-type semiconductor material.

The organic power-generating layer of the present invention can be prepared, for example, by dissolving the n-type semiconductor material of the present invention and the organic p-type semiconductor material mentioned above in an organic solvent, and forming a thin film from the obtained solution on a substrate using a known thin-film forming technique, such as spin coating, casting, dipping, inkjet, and screen printing.

In thin-film formation of an organic power-generating layer, the fullerene derivative of the present invention exhibits excellent compatibility with organic p-type semiconductor materials (preferably, P3HT or PTB7) and suitable self-aggregating properties. This makes it easy to produce an organic power-generating layer comprising the fullerene derivative of the present invention as an n-type semiconductor material and an organic p-type semiconductor material in a bulk heterojunction structure.

Organic Thin-Film Solar Cell

The organic thin-film solar cell of the present invention comprises the organic power-generating layer of the present invention described above.

Thus, the organic thin-film solar cell of the present invention exhibits high conversion efficiency.

The structure of the organic thin-film solar cell is not particularly limited, and may be the same as that of a known organic thin-film solar cell. The organic thin-film solar cell of the present invention can be produced in accordance with a known method for producing an organic thin-film solar cell.

One example of the organic thin-film solar cell comprising the fullerene derivative is a solar cell comprising, disposed on a substrate in series, a transparent electrode (negative electrode), a charge transport layer on the negative electrode side, an organic power-generating layer, a charge transport layer on the positive electrode side, and an opposite electrode (positive electrode). The organic power-generating layer is preferably a thin-film semiconductor layer (i.e., a photoelectric conversion layer) that comprises an organic p-type semiconductor material and the fullerene derivative of the present invention as an n-type semiconductor material, and that is formed in a bulk heterojunction structure.

In solar cells having the structure described above, known materials can suitably be used as materials for layers other than the organic power-generating layer. Specific examples of electrode materials include aluminium, gold, silver, copper, and indium tin oxide (ITO). Examples of charge transport layer materials include PFN (poly[9,9-bis(3'-(N,N-dimethylamino)propyl-2,7-fluorene)-alt-2,7-(9,9-dioctylfluorene)]) and MoO$_3$(molybdenum oxide).

Photosensor

As described above, the photoelectric conversion layer obtained by the present invention can effectively function as an image sensor light-receiving part of advanced digital cameras. As compared with conventional photosensors using a silicon photodiode, a photosensor using the photoelectric conversion layer obtained by the present invention can receive an image in a well-lit area without overexposure as well as a clear image in a poorly lit area. This makes it possible to obtain an image with higher quality than those of conventional cameras. A photosensor comprises a silicon substrate, electrodes, a light-receiving part consisting of a photoelectric conversion layer, a color filter, and a microlens. The light-receiving part can be about several hundred nanometers in thickness, a fraction of the thickness of conventional silicon photodiodes.

EXAMPLES

The following Examples describe the present invention in more detail. However, the present invention is not limited to the Examples.

The annotation of the symbols and abbreviations used in the Examples is shown below. In addition, symbols and abbreviations typically used in the technical field to which the present invention pertains may also be used throughout this specification.

The aldehyde compounds used as a starting material in synthesizing fullerene derivatives in the following Examples were synthesized in accordance with the method disclosed in the literature below.

1) 3-Oxaheptanal: n-BuOCH$_2$CHO
Yuichi Yamamoto, Yakugaku Zasshi (Journal of the Pharmaceutical Society of Japan), 1953, vol. 73, p. 938

2) 3,6,9-Trioxadacanal: CH$_3$O(CH$_2$CH$_2$O)$_2$CH$_2$CHO
J. M. Harris et al., J. Polym. Sci. Part A, 1987, vol. 25, p. 2447

3) 4-Ethyl-heptanal: CH$_3$(CH$_2$)$_3$CH(C$_2$H$_5$)CH$_2$CHO
Wei You et al., Macromolecules, 2010, vol. 43, p. 811

Synthesis Example 1

Amino Acid Derivative: Synthesis of 2-(Phenylamino)-Octanoic Acid

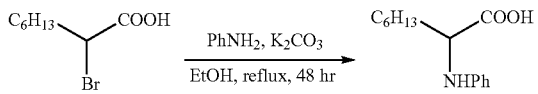

An ethanol solution (3 mL) of 2-bromooctanoic acid (1.28 g, 5.74 mmol), aniline (534 mg, 5.74 mmol), and potassium carbonate (800 mg, 5.74 mmol) was heated under reflux for 48 hours. After cooling, the reaction product solution was diluted with water and extracted with ether.

Additionally, the obtained aqueous phase was adjusted to a pH of 3 with 1N hydrochloric acid and extracted with ethyl acetate.

The organic phase was dried over magnesium sulfate and concentrated under reduced pressure, thereby obtaining 982 mg (72.8%) of the target product.

$^1$H-NMR (acetone-d$_6$) δ: 0.85 (3H, t, J=6.9 Hz), 1.14-1.54 (8H, m), 1.68-1.90 (2H, m), 2.83 (2H, bs), 3.99 (1H, d-d, J=7.2, 5.6 Hz), 6.58 (1H, t, J=7.3 Hz), 6.64 (2H, d, J=7.6 Hz), 7.06 (2H, d-d, J=7.3, 7.6 Hz).

Synthesis Example 2

Amino Acid Derivative: Synthesis of N-Phenyl-2-Phenylglycine

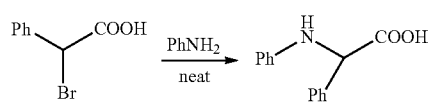

2-bromophenylacetic acid (2.15 g, 10.0 mmol) and aniline (4.09 g, 44.0 mmol) were heated at 100° C. for 72 hours in the absence of a solvent.

After cooling, the reaction mixture was diluted with ethyl acetate and extracted with 5% sodium hydroxide.

The obtained aqueous phase was adjusted to a pH of 4 with 1N hydrochloric acid and extracted with ethyl acetate.

The organic phase was dried over magnesium sulfate and concentrated under reduced pressure.

The obtained crude product was recrystallized with water-ethanol, thereby obtaining 560 mg (24.0%) of the target product.

$^1$H-NMR (acetone-d$_6$) δ: 2.02 (1H, bs), 5.15 (1H, s), 6.57 (1H, t, J=7.3 Hz), 6.67 (2H, d, J=8.8 Hz), 7.03 (2H, t, J=8.2 Hz), 7.27 (1H, t, J=7.3 Hz), 7.34 (2H, t, J=8.1 Hz), 7.55 (2H, d, J=7.8 Hz).

Synthesis Example 3

Synthesis of Compound 1

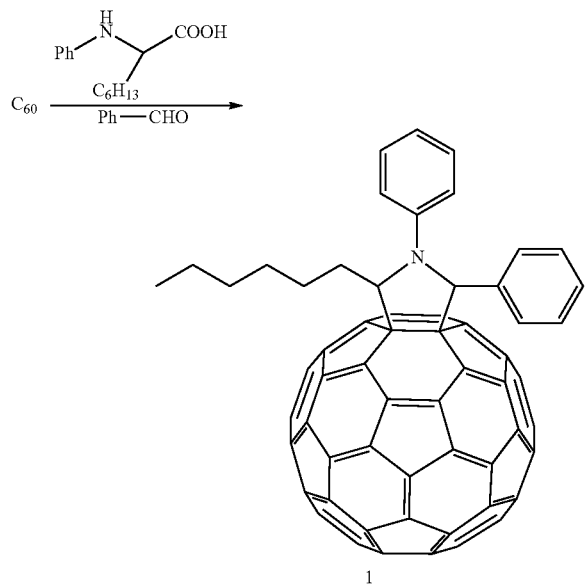

1

A chlorobenzene solution (150 mL) of 2-(phenylamino)-octanoic acid (118 mg, 0.5 mmol), benzaldehyde (1 mL), and a fullerene (360 mg, 0.5 mmol) was heated under reflux for 48 hours.

The reaction product solution was concentrated under reduced pressure, and the reaction product was purified by column chromatography (SiO$_2$, hexane-toluene=100:1 to 20:1), followed by further purification by HPLC (Buckyprep: toluene), thereby obtaining 105 mg (17.0%) of the target product (purity: 99% or more).

$^1$H-NMR (CDCl$_3$) δ: 0.82 (3H, t, J=7.2 Hz), 1.08-1.44 (6H, m), 1.46-1.58 (1H, m), 1.58-1.72 (1H, m), 2.22-2.34 (1H, m), 2.76-3.90 (1H, m), 5.67 (1H, d, J=9.2 Hz), 6.28 (1H, s), 6.95-7.05 (1H, m), 7.10-7.40 (7H, m), 7.66 (2H, d, J=7.6 Hz).

MS (FAB) m/z 1000 (M+). HRMS calcd for C$_{80}$H$_{25}$N 999.19870; found 999.2017.

Synthesis Example 4

Synthesis of Compound 2

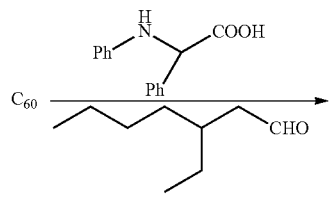

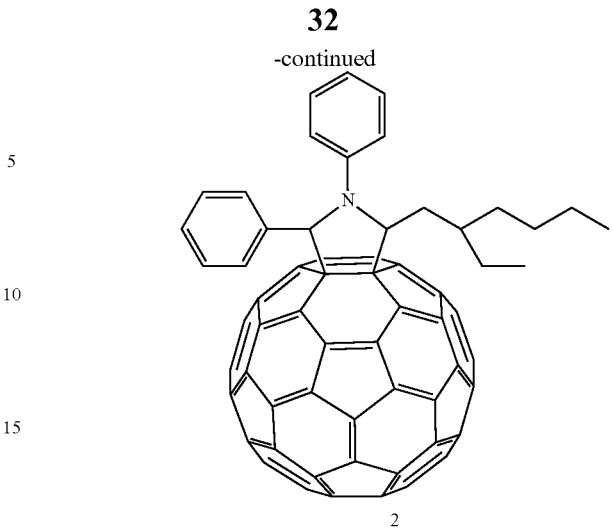

2

A chlorobenzene solution (200 mL) of N-phenyl-2-phenylglycine (112 mg, 0.5 mmol), 4-ethylheptanal (142 mg, 1 mmol), and a fullerene (360 mg, 0.5 mmol) was heated under reflux for 48 hours.

The reaction product solution was concentrated under reduced pressure, and the reaction product was purified by column chromatography (SiO$_2$, hexane-toluene=100:1 to 20:1), thereby obtaining 154.5 mg (30.0%) of the target product (purity: 99% or more).

$^1$H-NMR (CDCl$_3$) δ: 0.70-1.00 (7H, m), 1.00-1.68 (8H, m), 1.99-2.13 (1H, m), 2.80-2.93 (1H, m), 5.62-5.75 (1H, m), 6.28 (1H, s), 6.95-7.08 (1H, m), 7.10-7.40 (7H, m), 7.67 (2H, d, J=7.8 Hz).

MS (FAB) m/z 1028 (M+). HRMS calcd for C$_{82}$H$_{28}$N 1027.2300; found 1027.2290.

Synthesis Example 5

Synthesis of Compound 3

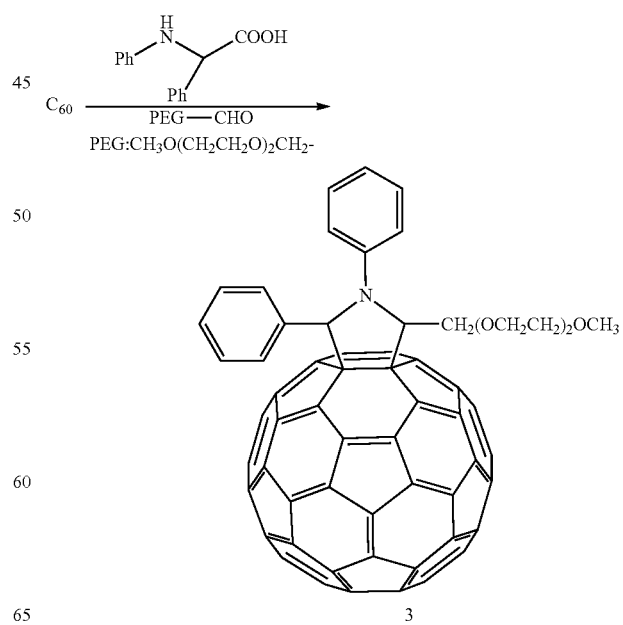

3

A chlorobenzene solution (150 mL) of N-phenyl-2-phenylglycine (112 mg, 0.5 mmol), 3,6,9-trioxadecanal (162 mg, 1 mmol), and a fullerene (360 mg, 0.5 mmol) was heated under reflux for 72 hours.

The reaction product solution was concentrated under reduced pressure, and the reaction product was purified by column chromatography ($SiO_2$, toluene-toluene:ethyl acetate=25:1), followed by further purification by HPLC (Buckyprep: toluene), thereby obtaining 217 mg (40.0%) of the target product (purity: 99% or more).

$^1$H-NMR ($CDCl_3$) δ: 3.35 (3H, s), 3.45-3.73 (8H, m), 4.30 (1H, d, J=10.0 Hz), 4.46 (1H, d-d, J=10.0, 5.2 Hz), 5.87 (1H, d, J=5.2 Hz), 6.78 (1H, s), 6.95-7.05 (1H, m), 7.15-7.40 (7H, m), 7.70 (2H, d, J=8.0 Hz).

MS (FAB) m/z 1047 (M+). HRMS calcd for $C_{80}H_{26}NO_3$ (M+1) 1048.1913; found 1048.1897.

Synthesis Example 6

Synthesis of Compound 4

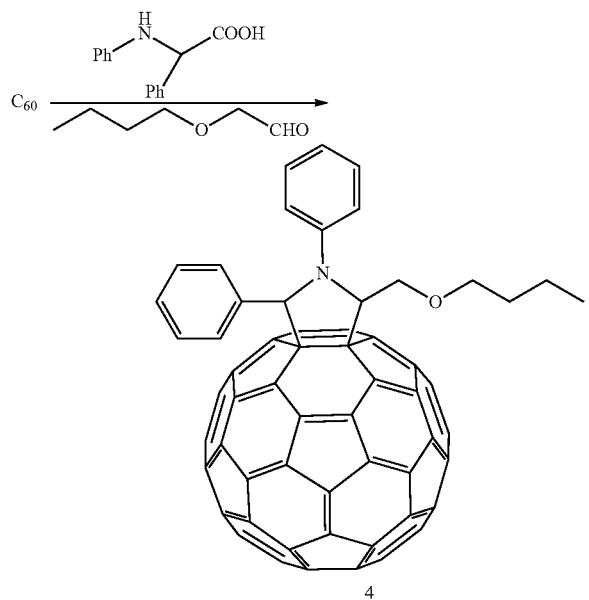

A chlorobenzene solution (150 mL) of N-phenyl-2-phenylglycine (112 mg, 0.5 mmol), 3-oxaheptanal (116 mg, 1 mmol), and a fullerene (360 mg, 0.5 mmol) was heated under reflux for 48 hours.

The reaction product solution was concentrated under reduced pressure, and the reaction product was purified by column chromatography ($SiO_2$, hexane:toluene=3:1), thereby obtaining 220.9 mg (44.1%) of the target product (purity: 99% or more).

$^1$H-NMR ($CDCl_3$) δ: 0.92 (3H, t, J=7.2 Hz), 1.38-1.52 (2H, m), 1.52-1.70 (2H, m), 3.30-3.42 (1H, m), 3.42-3.52 (1H, m), 4.20 (1H, d-d, J=10.0, 1.6 Hz), 4.39 (1H, d-d, J=10.0, 4.4 Hz), 5.85 (1H, d-d, J=4.4, 1.6 Hz), 6.80 (1H, s), 6.96-7.05 (1H, m), 7.10-7.37 (7H, m), 7.70 (2H, d, J=7.6 Hz).

MS (FAB) m/z 1002 (M+). HRMS calcd for $C_{79}H_{23}NO$ 1001.17796; found 1001.1790.

Synthesis Example 7

Synthesis of Compound 5

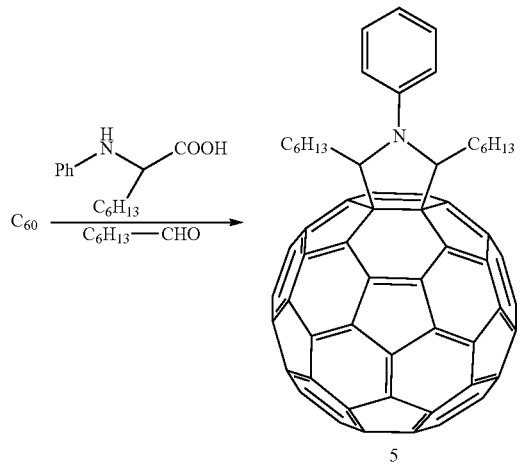

A chlorobenzene solution (150 mL) of 2-(phenylamino)-octanoic acid (118 mg, 0.5 mmol), heptanal (2 mL), and a fullerene (360 mg, 0.5 mmol) was heated under reflux for 48 hours.

The reaction product solution was concentrated under reduced pressure, and the reaction product was purified by column chromatography ($SiO_2$, hexane-toluene=100:1 to 20:1), followed by further purification by HPLC (Buckyprep: toluene), thereby obtaining 113 mg (22.4%) of the target product (purity: 99% or more).

$^1$H-NMR ($CDCl_3$) δ: 0.80 (6H, t, J=7.0 Hz), 1.10-1.39 (12H, m), 1.52-1.78 (4H, m), 2.32-2.56 (4H, m), 5.16 (2H, m), 7.14-7.24 (1H, m), 7.42-7.56 (4H, m).

MS (FAB) m/z 1008 (M+). HRMS calcd for $C_{80}H_{33}N$ 1007.26130; found 1007.2620.

Synthesis Example 8

Synthesis of Compound 6

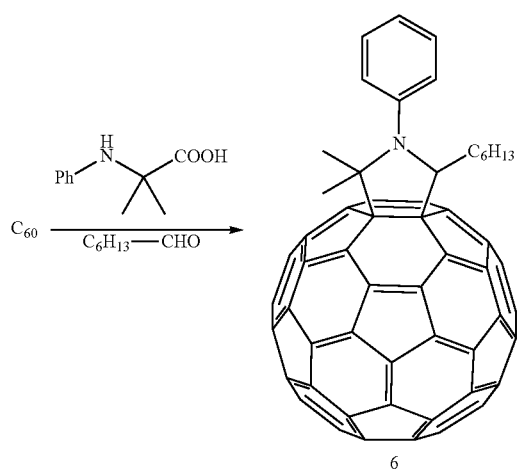

A chlorobenzene solution (150 mL) of N-phenyl-2-methyl alanine (90 mg, 0.5 mmol), heptanal (1 mL), and a fullerene (360 mg, 0.5 mmol) was heated under reflux for 48 hours.

The reaction product solution was concentrated under reduced pressure, and the reaction product was purified by column chromatography (SiO$_2$, hexane-toluene=100:1 to 10:1), thereby obtaining 211.9 mg (44.5%) of the target product (purity: 99% or more).

$^1$H-NMR (CDCl$_2$) δ: 0.76 (3H, t, J=7.0 Hz), 1.05-1.30 (6H, m), 1.55-1.70 (1H, m), 1.70-1.85 (1H, m), 2.14-2.38 (2H, m), 5.34 (1H, d-d, J=7.6, 2.4 Hz), 7.36 (1H, t, J=7.2 Hz), 7.47-7.63 (4H, m).

MS (FAB) m/z 952 (M+). HRMS calcd for C$_{76}$H$_{25}$N 951.19870; found 951.1990.

Synthesis Example 9

Synthesis of Compound 7

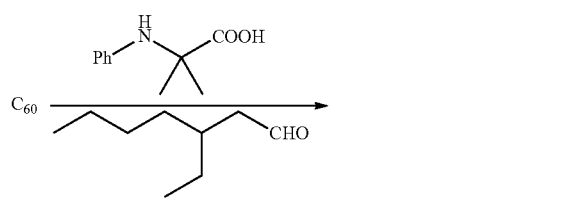

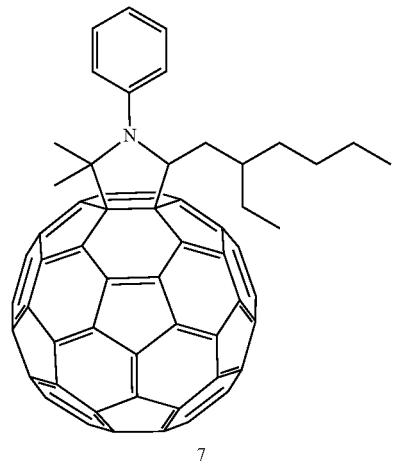

7

A chlorobenzene solution (300 mL) of N-phenyl-2-methyl alanine (180 mg, 1.0 mmol), 4-ethylheptanal (0.5 mL), and a fullerene (720 mg, 1.0 mmol) was heated under reflux for 48 hours.

The reaction product solution was concentrated under reduced pressure, and the reaction product was purified by column chromatography (SiO$_2$, hexane-toluene=100:1), followed by further purification by HPLC (Buckyprep: toluene), thereby obtaining 276 mg (28.2%) of the target product (purity: 99% or more).

$^1$H-NMR (CDCl$_3$) δ: 0.66 (1.5H, t, J=7.3 Hz), 0.70-0.75 (3H, m), 0.87 (1.5H, t, J=7.3 Hz), 0.94-1.66 (9H, m), 1.86-1.96 (1H, m), 2.22-2.36 (1H, m), 5.39-5.45 (1H, m), 7.37 (1H, t, J=8.2 Hz), 7.51 (2H, d-d, J=8.2, 8.2 Hz), 7.59 (2H, d, J=8.2 Hz).

Synthesis Example 10

Synthesis of Compound 8

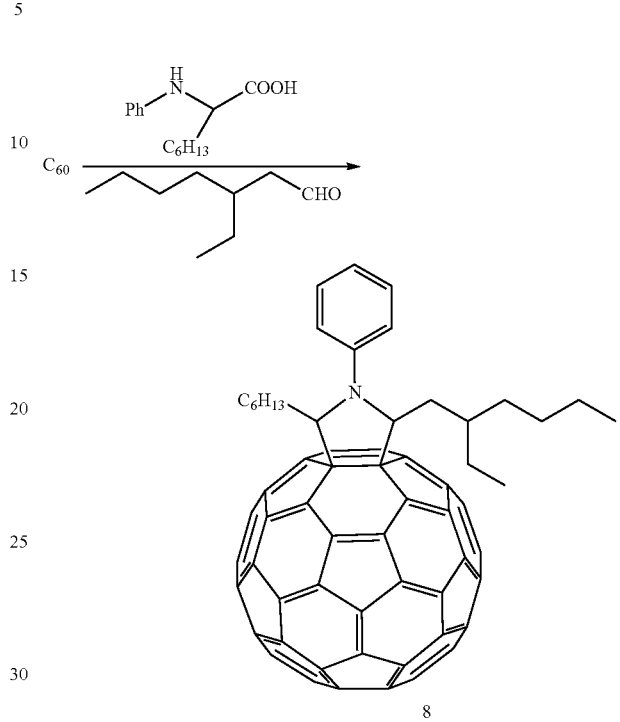

8

A chlorobenzene solution (150 mL) of 2-(phenylamino)-octanoic acid (118 mg, 0.5 mmol), 4-ethylheptanal (1 mL), and a fullerene (360 mg, 0.5 mmol) was heated under reflux for 15 hours.

The reaction product solution was concentrated under reduced pressure, and the reaction product was purified by column chromatography (SiO$_2$, hexane-toluene=100:1 to 30:1), followed by further purification by HPLC (Buckyprep: toluene), thereby obtaining 58.0 mg (11.0%) of the target product (purity: 99% or more).

$^1$H-NMR (CDCl$_3$) δ: 0.70-0.90 (9H, m), 0.90-1.90 (18H, m), 2.30-2.60 (3H, m), 5.17 (1H, d-d, J=7.5, 3.0 Hz), 5.31 (1H, d-d, J=8.5, 3.0 Hz), 7.10-7.30 (1H, m), 7.40-7.60 (4H, m).

Synthesis Example 11

Synthesis of Compound 9

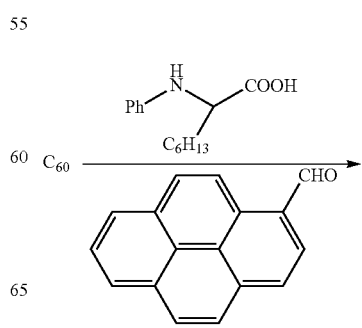

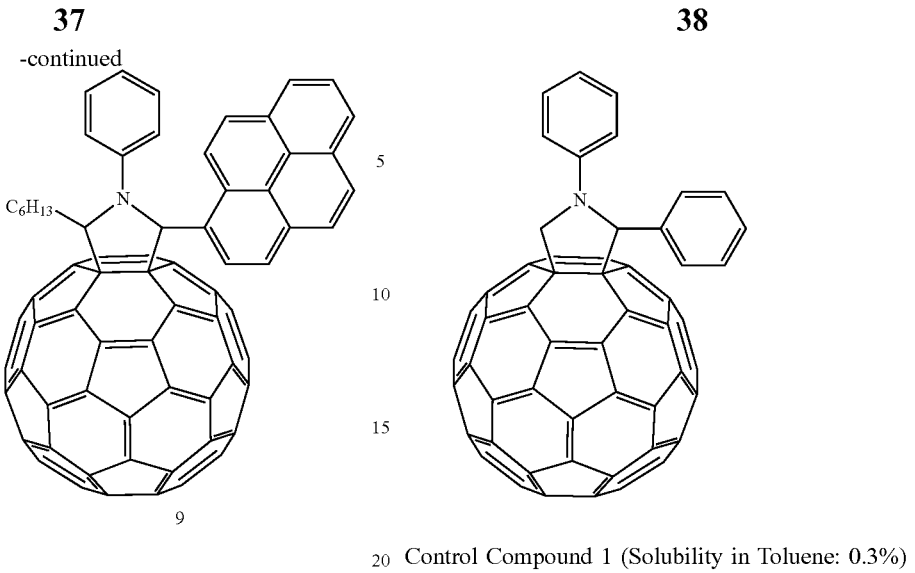

9

A chlorobenzene solution (150 mL) of 2-(phenylamino)-octanoic acid (118 mg, 0.5 mmol), 1-pyrene aldehyde (150 mg, 0.5 mmol), and a fullerene (360 mg, 0.5 mmol) was heated under reflux for 48 hours.

The reaction product solution was concentrated under reduced pressure, and the reaction product was purified by column chromatography ($SiO_2$, hexane-toluene=20:1 to 5:1), followed by further purification by HPLC (Buckyprep: toluene), thereby obtaining 99.0 mg (17.6%) of the target product (purity: 99% or more).

$^1$H-NMR ($CDCl_3$) δ: 0.83 (3H, t, J=8.0 Hz), 1.10-1.50 (6H, m), 1.50-1.85 (2H, m), 2.30-2.50 (1H, m), 3.00-3.15 (1H, m), 5.78-5.89 (1H, m), 6.91 (1H, t, J=7.0 Hz), 7.06-7.32 (4H, m), 7.50 (1H, s), 7.90-8.10 (4H, m), 8.10-8.25 (3H, m), 8.58 (1H, d, J=9.6 Hz), 8.90 (1H, d, J=9.6 Hz).

MS (FAB) m/z 1024 (M+). HRMS calcd for $C_{90}H_{30}N$ (M+1) 1024.2378; found 1024.2392.

Test Example 1

Solubility (Measured with a Toluene Solution)

The solubility of each fullerene derivative was calculated from the absorbance measured with an ultraviolet-visible absorptiometer.

In advance, the absorbance of the fullerene derivatives of a predetermined concentration was measured to determine the molar extinction coefficient of each compound.

A supersaturated toluene solution of a fullerene derivative was prepared. A predetermined amount of the supernatant of this solution was taken out, and its absorbance was measured.

From the measured absorbance value and the molar extinction coefficient, the concentration of the supernatant of the supersaturated toluene solution was determined.

Control Compounds: two compounds that are fullerene derivatives with no substituent at position 5 represented by the following chemical formulas were used in comparison.

Control Compound 1 (Solubility in Toluene: 0.3%)

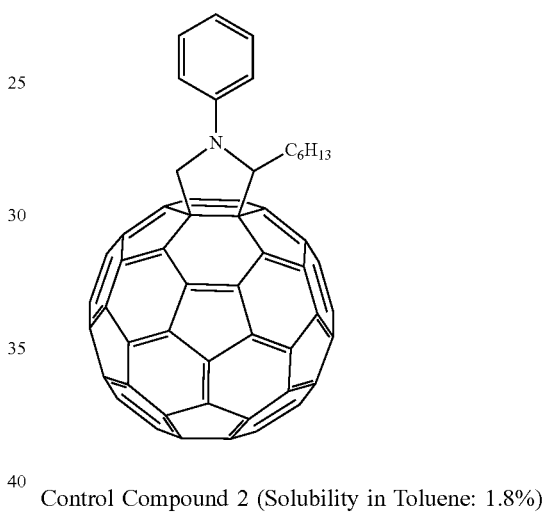

Control Compound 2 (Solubility in Toluene: 1.8%)
Compound 1: Solubility in Toluene 0.5%
Compound 2: Solubility in Toluene 1.0%
Compound 3: Solubility in Toluene 0.5%
Compound 4: Solubility in Toluene 0.5%
Compound 5: Solubility in Toluene 2.4%
Compound 8: Solubility in Toluene 7.0%

When the control compounds having a substituent at position 2 (control compound 1: phenyl, control compound 2: hexyl) additionally had an alkyl group at position 5, their solubility was significantly increased.

Test Example 2

Solar cells were prepared using the fullerene derivatives obtained in Synthesis Examples and the control compounds as an n-type semiconductor material in accordance with the following method, and the function of the cells was evaluated.

The following materials were used: PTB7 for an organic p-type semiconductor material, PFN (poly[9,9-bis(3'-(N,N-dimethylamino)propyl-2,7-fluorene)-alt-2,7-(9,9-dioctylfluorene)]) and $MoO_3$ (molybdenum oxide) for charge transport layer materials, and ITO (indium tin oxide) (negative electrode) and aluminium (positive electrode) for electrodes.

(1) Preparation of Solar Cell for Testing

Solar cells for testing were prepared in accordance with the following procedure.

1) Pretreatment of Substrate

An ITO patterning glass plate was placed in a plasma cleaner, and the surface of the substrate was washed with generated plasma for 10 minutes while oxygen gas was allowed to flow in.

2) Preparation of PFN Thin Film (Charge Transport Layer on Negative Electrode Side)

A PFN thin film was formed using a PFN methanol solution (2% w/v) on the pretreated ITO glass plate with an ABLE/ASS-301 spin-coating-film-forming device. The formed PFN thin film had a thickness of about 10 nm.

3) Preparation of Organic Semiconductor Film (Organic Power-Generating Layer)

With the substrate placed in a glove box, the PFN thin film was spin-coated with a solution containing PTB7 and the fullerene derivative dissolved in chlorobenzene beforehand, and diiodooctane (3% v/v relative to chlorobenzene), with a MIKASA/MS-100 spin-coating film-forming device at 1,000 rpm for 2 minutes to form an organic semiconductor thin film (organic power-generating layer) of about 90 to 110 nm. A laminate was thus obtained.

4) Vacuum Deposition of Charge Transport Layer on Positive Electrode Side and Vacuum Deposition of Metal Electrode The prepared laminate was placed on a mask inside a compact high-vacuum evaporator. An $MoO_3$ layer (10 nm) as a charge transport layer on the positive electrode side and an aluminium layer (80 nm) as a metal electrode were deposited on the laminate in series with the high-vacuum evaporator.

(2) Current Measurement by Pseudo Solar Light Irradiation

Current measurement using pseudo solar light irradiation was conducted by using a SourceMeter, current-voltage measuring software, and a solar simulator.

The solar cells for testing prepared in section (1) were irradiated with pseudo solar light of 100 mW, and the generated current and voltage were measured. Energy conversion efficiency was then calculated from the following equation.

Table 1 shows the measurement results of short-circuit current, open voltage, fill factor (FF), and conversion efficiency. The conversion efficiency is a value determined from the following equation.

Conversion efficiency $\eta$ (%)=$FF(V_{oc} \times J_{sc}/P_{in}) \times 100$

The table shows the following results.

FF: Fill Factor, $V_{oc}$: Open Voltage, $J_{sc}$: Short-circuit Current, $P_{in}$: Intensity of Incident Light (Density).

TABLE 1

| Fullerene Derivative | P-type Semiconductor Material | Short-circuit Current (mA/cm$^2$) | Open Voltage (V) | FF | Conversion Efficiency (%) |
|---|---|---|---|---|---|
| Control Compound 1 | PTB7 | 15.48 | 0.75 | 0.63 | 7.34 |
| Control Compound 2 | PTB7 | 14.21 | 0.76 | 0.67 | 7.27 |
| Compound 1 | PTB7 | 14.52 | 0.79 | 0.63 | 7.28 |
| Compound 2 | PTB7 | 14.96 | 0.82 | 0.61 | 7.48 |
| Compound 3 | PTB7 | 13.66 | 0.79 | 0.65 | 6.96 |
| Compound 4 | PTB7 | 14.86 | 0.79 | 0.60 | 7.00 |
| Compound 5 | PTB7 | 13.86 | 0.84 | 0.56 | 6.48 |
| Compound 6 | PTB7 | 14.22 | 0.81 | 0.60 | 6.87 |
| Compound 7 | PTB7 | 14.20 | 0.82 | 0.59 | 6.84 |
| Compound 9 | PTB7 | 12.88 | 0.79 | 0.51 | 5.13 |

Compared with the control compounds 1 and 2, which have, no substituent at position 5 of their pyrrolidine ring, solar cells using the compounds of the present invention all exhibited an increased open voltage due to the presence of an alkyl group or the like, which is an electron-donating group, at position 5.

Additionally, in response to the number of the alkyl substituents, open voltage was increased.

Although there is some literature that mentions substituents of phenyl contained in a fullerene derivative structure and open voltage (literature 1) to 4) listed below), there have been no findings concerning the number and type of substituents introduced into a pyrrolidine-containing derivative.

Additionally, there have been no findings concerning the structure and performance of solar cells using a fullerene derivative whose pyrrolidine ring has substituents at positions 1, 2, and 5.

Test Example 3

The LUMO level of the fullerene derivatives obtained in Synthesis Examples and the control compounds was estimated from the measured values in cyclic voltammetry (CV).

Measurement Method

The measurement was performed in accordance with the experiment section in M. Karakawa et al., Journal of Material Chemistry A, 2014, vol. 2, p. 20889.

Measurement Device: BAS CV-50W Voltammetric Analyzer

Measurement Solvent: Chlorobenzene:Acetonitrile=5:1

Supporting Electrolyte: n-$Bu_4NPF_6$ concentration 0.1 mol/L

The LUMO level is calculated from the half-wave potential $E_{1/2}^1$ (Fc/Fc$^+$ benchmark) of the first reduction wave measured by CV (3-electrode system) using the following equation.

$E_{LUMO} = -(E_{1/2}^1 + 4.8)$eV

TABLE 2

| Compound | $E^1_{1/2}$ (V vs Fc/Fc$^{++}$) | LUMO (eV) | $V_{oc}$ [V] |
|---|---|---|---|
| Compound 1 | −1.16 | −3.64 | 0.79 |
| Compound 4 | −1.17 | −3.63 | 0.79 |
| Compound 3 | −1.17 | −3.63 | 0.79 |
| Compound 5 | −1.17 | −3.63 | 0.84 |
| Compound 6 | −1.17 | −3.63 | 0.81 |
| Compound 2 | −1.17 | −3.63 | 0.82 |
| Control Compound 1 | −1.13 | −3.67 | 0.75 |
| Control Compound 2 | −1.14 | −3.66 | 0.76 |
| [60]PCBM | −1.13 | −3.67 | 0.736 |

The invention claimed is:

1. A fullerene derivative represented by formula (1)

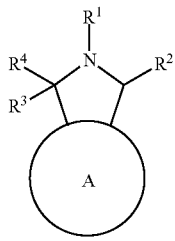

(1)

wherein
R$^1$ represents aryl optionally substituted with at least one substituent,
R$^2$ represents an organic group,
R$^3$ represents an organic group, with the proviso that at least one of R$^2$ and R$^3$ is alkyl optionally substituted with at least one substituent or alkyl ether optionally substituted with at least one substituent,
R$^4$ represents a hydrogen atom or an organic group, and
ring A represents a fullerene ring, and
wherein the fullerene derivative has
(1) an LUMO level of −3.65 eV or more, and
(2) a solubility in toluene at room temperature of 0.5% or more.

2. The fullerene derivative according to claim 1, wherein R$^1$ is aryl optionally substituted with at least one substituent selected from the group consisting of fluorine, chlorine, bromine, iodine, methyl, methoxy, and cyano.

3. The fullerene derivative according to claim 1, wherein R$^1$ is phenyl optionally substituted with at least one fluorine atom.

4. The fullerene derivative according to claim 1, wherein R$^1$ is alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

5. The fullerene derivative according to claim 1, wherein R$^3$ and R$^4$ are identical or different and each represent hydrogen, alkyl optionally substituted with at least one substituent, alkenyl optionally substituted with at least one substituent, alkynyl optionally substituted with at least one substituent, aryl optionally substituted with at least one substituent, ether optionally substituted with at least one substituent, or ester optionally substituted with at least one substituent.

6. The fullerene derivative according to claim 1, wherein ring A is a C$_{60}$ fullerene or a C$_{70}$ fullerene.

7. An n-type semiconductor material comprising the fullerene derivative according to claim 1.

8. An organic thin-film solar cell comprising the n-type semiconductor material according to claim 7.

9. An organic power-generating layer comprising the n-type semiconductor material according to claim 8.

10. A photoelectric conversion element comprising the organic power-generating layer according to claim 9.

11. The photoelectric conversion element according to claim 10, which is an organic thin-film solar cell.

* * * * *